(12) United States Patent
Lukŝic et al.

(10) Patent No.: US 11,672,465 B2
(45) Date of Patent: Jun. 13, 2023

(54) METHODS, SYSTEMS, DEVICES, AND COMPONENTS FOR VISUALIZING ELECTROGRAPHIC FLOW (EGF)

(71) Applicant: Ablacon Inc., Wheat Ridge, CO (US)

(72) Inventors: David Emanuel Lukŝic, Munich (DE); Philip Haeusser, Munich (DE); Peter Ruppersberg, Blonay (CH)

(73) Assignee: Ablacon Inc., Wheat Ridge, CO (US)

( * ) Notice: Subject to any disclaimer, the term of this patent is extended or adjusted under 35 U.S.C. 154(b) by 373 days.

(21) Appl. No.: 16/918,588

(22) Filed: Jul. 1, 2020

(65) Prior Publication Data

US 2021/0000369 A1    Jan. 7, 2021

Related U.S. Application Data

(60) Provisional application No. 62/869,457, filed on Jul. 1, 2019.

(51) Int. Cl.
| | |
|---|---|
| *A61B 5/364* | (2021.01) |
| *A61B 5/00* | (2006.01) |
| *A61B 34/20* | (2016.01) |
| *A61B 5/055* | (2006.01) |
| *A61B 18/14* | (2006.01) |
| *A61B 6/03* | (2006.01) |
| *A61B 5/287* | (2021.01) |
| *A61B 5/339* | (2021.01) |
| *A61B 18/00* | (2006.01) |
| *A61B 6/00* | (2006.01) |

(52) U.S. Cl.
CPC .............. *A61B 5/364* (2021.01); *A61B 5/055* (2013.01); *A61B 5/287* (2021.01); *A61B 5/339* (2021.01); *A61B 5/6858* (2013.01); *A61B 5/6859* (2013.01); *A61B 6/032* (2013.01); *A61B 18/1492* (2013.01); *A61B 34/20* (2016.02); *A61B 6/487* (2013.01); *A61B 2018/00351* (2013.01); *A61B 2018/00577* (2013.01); *A61B 2034/2065* (2016.02)

(58) Field of Classification Search
None
See application file for complete search history.

(56) References Cited

U.S. PATENT DOCUMENTS

2017/0065198 A1 *  3/2017  Ruppersberg ........ A61B 5/6852

OTHER PUBLICATIONS

Cabral et al, Imaging vector fields using line integral convolution. Technical report, Lawrence Livermore National Lab., CA (United States), 1993.

(Continued)

*Primary Examiner* — Ankit D Tejani
(74) *Attorney, Agent, or Firm* — McDermott Will & Emery

(57) ABSTRACT

Electrographic flow mapping (EGF mapping) is a technique used for aiding catheter ablation when treating atrial fibrillation. Visualizing EGF fields during a cardiac catherization and ablation procedure is an important and necessary part of conducting the procedure. Several different visualization methods are described and disclosed herein that may be employed to visualize EGF fields and maps, including quiver plots, streamline plots, particle plots, particle trail plots, moving particle plots, and moving and fading particle plots.

34 Claims, 23 Drawing Sheets

(16 of 23 Drawing Sheet(s) Filed in Color)

(56) References Cited

OTHER PUBLICATIONS

Catmull et al, a class of local interpolating splines. U Computer aided geometric design stranice 317-326, Elsevier, 1974.
McEwan et al, Efficient computational noise in glsl Journal of Graphics Tools, 16(2):85-94, 2012.
Paulus et al, 2016 esc guidelines for the management of atrial fibrillation developed in collaboration with eacts. Europ.Jour. of cardio-thoracic surgery, 50 (5):e1-e88, 2016.
Bellmann et al, . Identif.of active atrial fibr. srcs and their discrim. from passive rotors using electro. flow map. Clinical Research in Cardiology, 107(11):1021-1032, 2018.

* cited by examiner

METHODS, SYSTEMS, DEVICES, AND COMPONENTS FOR VISUALIZING ELECTROGRAPHIC FLOW (EGF)

RELATED APPLICATIONS

This application is related to, and claims priority and other benefits from, U.S. Provisional Patent Application Ser. No. 62/869,457 entitled "Methods, Systems, Devices and Components for Visualization of Electrographic Flow (EGF)" to Lukšić et al. filed Jul. 1, 2019 (hereafter "the '457 patent application"). The entirety of the '457 patent application is hereby incorporated by reference herein.

FIELD OF THE INVENTION

Various embodiments described and disclosed herein relate to the field of medicine generally, and more particularly to diagnosing and treating cardiac rhythm disorders in a patient's heart using electrophysiological mapping techniques.

BACKGROUND

Persistent atrial fibrillation (AF) is assumed to be caused by structural changes in atrial tissue, which can manifest themselves as multiwavelet re-entry and/or stable rotor mechanisms (see, e.g., De Groot M S et al., "Electropathological Substrate of Longstanding Persistent Atrial Fibrillation in Patients with Structural Heart Disease Epicardial Breakthrough," Circulation, 2010, 3: 1674-1682). Radio frequency (RF) ablation targeting such host drivers of AF is generally accepted as the best therapeutic approach. RF ablation success rates in treating AF cases are currently limited, however, by a lack of diagnostic tools that are capable of precisely determining the locations of such AF drivers. Better diagnostic tools would help reduce the frequency and extent of cardiac ablation procedures to the minimum amount required to treat AF, and would help balance the benefits of decreased fibrillatory burden against the morbidity of increased lesion load.

Methods exist to estimate the flow of action potentials in the heart, namely, electrographic flow (EGF), invented by Dr. Peter Ruppersberg. See, for example, Bellman et al., 2018. In such flow fields, sources of EGF can be identified. It was shown that the existence of such sources in patients with atrial fibrillation correlates with a patient's outcome after an ablation procedure.

During an ablation procedure, electrophysiologists aim at identifying structures that are ablation targets so as to ablate atrial tissue which drives atrial fibrillation.

It is important for the doctor to understand the general structure of a patient's atrial fibrillation patterns. EGF per se results in vector fields.

While one can detect points of interest such as sources or rotational phenomena, and show them as "heat maps", an additional method is necessary to convey the "big picture," for example to understand how multiple such phenomena interact with one another.

Classical methods represent flow fields with arrows. Arrows can be difficult for a human to grasp when EGF patterns become complicated.

What is needed are improved means and methods of visualizing EGF fields that reliably, intuitively, quickly, and accurately yield the precise locations of cardiac rhythm disorders in a patient's heart. Doing so would enable cardiac ablation procedures to be carried out with greater locational precision, and would result in higher rates of success in treating cardiac rhythm disorders such as AF.

SUMMARY

In one embodiment, there is provided a system configured to detect a location of a source of at least one cardiac rhythm disorder in a patient's heart, the system comprising an electrode mapping assembly comprising a plurality of electrodes and a plurality of arms or splines, the electrodes being mounted on or attached to the arms or splines, the electrode mapping assembly being configured to be deployed or opened inside the patient's heart such that at least some of the electrodes engage one or more sidewalls of the patients heart, each of the electrodes having a predetermined position on one of the arms or splines; a monitor or screen, and at least one computing device comprising at least one non-transitory computer readable medium configured to store instructions executable by at least one processor to determine the source and location of the cardiac rhythm disorder in the patient's heart, wherein the monitor or screen is operably connected to the computing device, and the computing device is configured to: (a) receive electrogram signals from the electrode mapping device while the electrode mapping assembly is deployed within the patient's heart to form a deployed 3D geometry of the electrode mapping assembly; (b) assign the predetermined positions of the electrodes on the mapping electrode assembly to their corresponding electrogram signals; (c) provide or generate a two-dimensional (2D) spatial map of the electrode positions; (d) for each or selected discrete times over which the electrogram signals are being processed, process the electrogram signals to generate a 2D electrographic flow map corresponding to the 2D spatial map of the electrode positions; and (e) project the generated 2D electrographic flow map onto a 3D representation of the deployed 3D geometry of the electrode mapping assembly on the monitor or screen to form a 3D electrographic flow map, the 3D electrographic flow map being configured to reveal the location of the source of the at least one cardiac rhythm disorder within the patient's heart so that a user can diagnose or treat the patient.

In another embodiment there is a provided a method of detecting a location of a source of at least one cardiac rhythm disorder in a patient's heart using a system comprising at least one computing device, the computing device comprising at least one non-transitory computer readable medium configured to store instructions executable by at least one processor to determine the source and location of the cardiac rhythm disorder in the patient's heart, the system further comprising a monitor or screen operably connected to the computing device and a mapping electrode assembly, the electrode mapping assembly comprising a plurality of electrodes and a plurality of arms or splines, the electrodes being mounted on or attached to the arms or splines, the electrode mapping assembly being configured to be deployed or opened inside the patient's heart such that at least some of the electrodes engage one or more sidewalls of the patients heart, each of the electrodes having a predetermined position on one of the arms or splines, the method comprising: (a) acquiring electrogram signals inside the patient's heart using the electrodes mounted on or attached to the mapping electrode assembly; (b) using the computing device, assigning positions or identifiers for each of the electrodes to corresponding individual electrogram signals; (c) using the computing device, providing or generating a two-dimensional (2D) spatial map of the electrode positions; (d) using the computing device, processing the electrogram signals to generate a 2D electrographic flow map corresponding to the 2D spatial map of the electrode positions, and (e) using the computing device, projecting the generated 2D electrographic flow map onto a 3D representation of the deployed 3D geometry of the electrode mapping assembly on the monitor or screen to form a 3D electrographic flow map, the 3D electrographic flow map being configured to reveal the location of the source of the at least one cardiac rhythm disorder so that a user can diagnose or treat the patient.

Further embodiments are disclosed herein or will become apparent to those skilled in the art after having read and understood the claims, specification and drawings hereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Different aspects of the various embodiments will become apparent from the following specification, drawings and claims in which:

The drawings are not necessarily to scale. Like numbers refer to like parts or steps throughout the drawings.

DETAILED DESCRIPTIONS OF SOME EMBODIMENTS

Described herein are various embodiments of systems, devices, components and methods for diagnosing and treating cardiac rhythm disorders in a patient's heart using electrophysiological mapping or electrographic flow (EGF) techniques, as well as imaging, navigation, cardiac ablation and other types of medical systems, devices, components, and methods. Various embodiments described and disclosed herein also relate to systems, devices, components and methods for discovering with enhanced precision the location(s) of the source(s) of different types of cardiac rhythm disorders and irregularities. Such cardiac rhythm disorders and irregularities, include, but are not limited to, arrhythmias, atrial fibrillation (AF or A-fib), atrial tachycardia, atrial flutter, paroxysmal fibrillation, paroxysmal flutter, persistent fibrillation, ventricular fibrillation (V-fib), ventricular tachycardia, atrial tachycardia (A-tach), ventricular tachycardia (V-tach), supraventricular tachycardia (SVT), paroxysmal supraventricular tachycardia (PSVT), Wolff-Parkinson-White syndrome, bradycardia, sinus bradycardia, ectopic atrial bradycardia, junctional bradycardia, heart blocks, atrioventricular block, idioventricular rhythm, areas of fibrosis, breakthrough points, focus points, re-entry points, premature atrial contractions (PACs), premature ventricular contractions (PVCs), and other types of cardiac rhythm disorders and irregularities.

Various embodiments of EGF techniques, methods, systems, devices, and components are described and disclosed herein, which involve the acquisition of intra-cardiac and/or body surface electrograms, and the subsequent processing and analysis of such electrograms to reveal the locations of sources of cardiac rhythm disorders in a patient's heart, such as rotors and sources that cause or contribute to AF. That is, many of the various techniques, methods, systems, devices, and components described and disclosed herein may be referred to collectively as pertaining to "EGF."

Systems and methods configured to detect in a patient's heart a location of a source of at least one cardiac rhythm disorder are disclosed herein. In the following description, for the purposes of explanation, numerous specific details are set forth in order to provide a thorough understanding of example embodiments or aspects. It will be evident, however, to one skilled in the art that an example embodiment may be practiced without necessarily using all of the disclosed specific details.

Figure 1A:
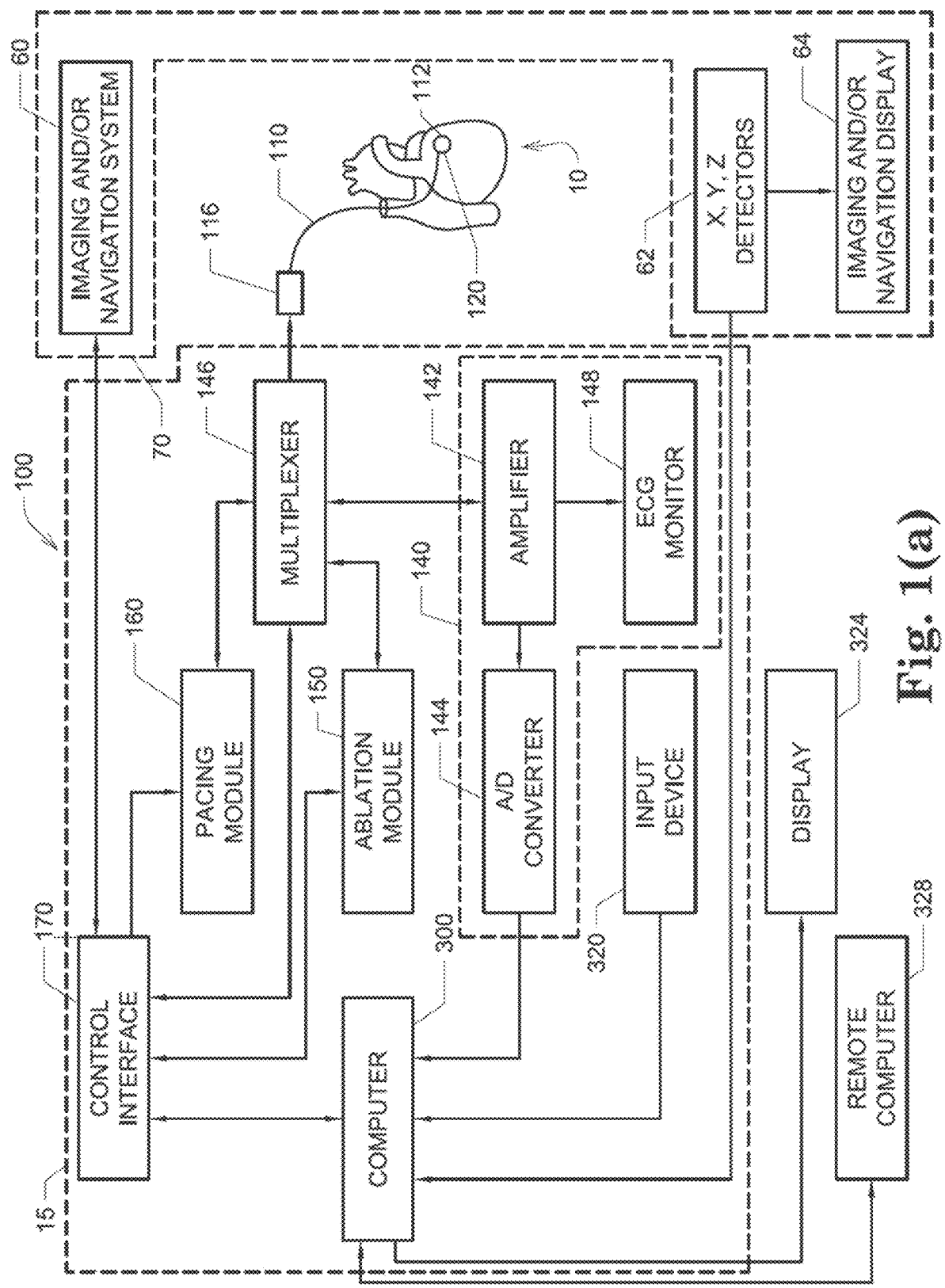
FIG. 1(a) shows one embodiment of a combined cardiac electrophysiological mapping (EP), pacing and ablation system 100.

Referring now to FIG. 1(a), there is illustrated one embodiment of a combined cardiac electrophysiological mapping (EP), pacing and ablation system 100. Note that in some embodiments system 100 may not include ablation module 150 and/or pacing module 160. Among other things, the embodiment of system 100 shown in FIG. 1(a) is configured to detect and reconstruct cardiac activation or electrographic flow ("EGF") information acquired from a patient's heart relating to cardiac rhythm disorders and/or irregularities, and is further configured to detect and discover the location of the source of such cardiac rhythm disorders and/or irregularities with enhanced precision relative to prior art techniques. In some embodiments, system 100 is further configured to treat the location of the source of the cardiac rhythm disorder or irregularity, for example by ablating the patient's heart at the detected location.

The embodiment of system 100 shown in FIG. 1(a) comprises five main functional units: electrophysiological mapping (EP mapping unit) 140 (which is also referred to herein as data acquisition device 140), ablation module 150, pacing module 160, imaging and/or navigation system 70, and computer or computing device 300. Data acquisition, processing and control system 15 comprises data acquisition device 140, ablation module 150, pacing module 160, control interface 170 and computer or computing device 300. Depending on how system 100 is configured, multiplexer 146 and/or control interface 170 may or may not be employed, or may be employed in a configuration different form that shown in FIG. 1(a).

In one embodiment, at least one computer or computing device or system 300 is employed to control the operation of one or more of systems, modules and devices 140, 150, 160, 170 and 70. Alternatively, the respective operations of systems, modules or devices 140, 150, 160, 170 and 70 may be controlled separately by each of such systems, modules and devices, or by some combination of such systems, modules and devices. Note that computer 300 may comprise multiple or distributed computers, again depending on the specifics of how system 100 is configured. For example, one computer may be employed to acquire and process signals or other data originating from catheter 100 while electrophysiological data ("EP data") are being collected from patient's heart 10, while another computer may be employed to process, analyze, and/or interpret the EP data at some point in time after they have been acquired.

Instead of being operably connected (e.g., through Bluetooth signals, a LAN or WAN network, or through the cloud), or directly connected, to computing device 300, data acquisition device 140 may be configured to provide as outputs therefrom saved or stored body surface electrogram signals, which can be, by way of example, saved or stored on a hard drive, in a memory, on a USB stick, or other suitable storage device, and where the saved or stored body surface electrogram signals are later or subsequently provided as inputs to computing device 300 for processing and analysis.

Computer or computing device 300 may be configured to receive operator inputs from an input device 320 such as a keyboard, mouse and/or control panel. Outputs from computer 300 may be displayed on display or monitor 324 or other output devices (not shown in FIG. 1(a)). Computer 300 may also be operably connected to a remote computer or analytic database or server 328. At least each of components, devices, modules and systems 60, 110, 140, 146, 148, 150, 170, 300, 324 and 328 may be operably connected to other components or devices by wireless (e.g., Bluetooth) or wired means. Data may be transferred between components, devices, modules or systems through hardwiring, by wireless means, or by using portable memory devices such as USB memory sticks.

During electrophysiological (EP) mapping procedures, multi-electrode catheter 110 (e.g., a basket EP mapping catheter) is typically introduced percutaneously into the patient's heart 10. Catheter 110 is passed through a blood vessel (not shown), such as a femoral vein or the aorta, and thence into an endocardial site such as the atrium or ventricle of the heart 10.

It is contemplated that other catheters, including other types of mapping or EP catheters, lasso catheters, pulmonary vein isolation (PVI) ablation catheters (which can operate in conjunction with sensing lasso catheters), ablation catheters, navigation catheters, and other types of EP mapping catheters such as EP monitoring catheters and spiral catheters may also be introduced into the heart, and that additional surface electrodes may be attached to the skin of the patient to record electrocardiograms (ECGs).

When system 100 is operating in an EP mapping mode, multi-electrode catheter 110 functions as a detector of intra-electrocardiac signals, while optional surface electrodes may serve as detectors of surface ECGs. In one embodiment, the analog signals obtained from the intracardiac and/or surface electrodes are routed by multiplexer 146 to data acquisition device 140, which comprises an amplifier 142 and an A/D converter (ADC) 144. The amplified or conditioned electrogram signals may be displayed by electrocardiogram (ECG) monitor 148. The analog signals are also digitized via ADC 144 and input into computer 300 for data processing, analysis and graphical display.

In one embodiment, catheter 110 is configured to detect cardiac activation or other information in the patient's heart 10, and to transmit the detected cardiac activation information to data acquisition device 140, either via a wireless or wired connection. In one embodiment that is not intended to be limiting with respect to the number, arrangement, configuration, or types of electrodes, catheter 110 includes a plurality of 64 electrodes, probes and/or sensors A1 through H8 arranged in an 8×8 grid that are included in electrode mapping assembly 120, which is configured for insertion into the patient's heart through the patient's blood vessels and/or veins. Other numbers, arrangements, configurations and types of electrodes in catheter 110 are, however, also contemplated. In most of the various embodiments, at least some electrodes, probes and/or sensors included in catheter 110 are configured to detect cardiac activation or electrical signals, and to generate electrocardiograms or electrogram signals, which are then relayed by electrical conductors from or near the distal end 112 of catheter 110 to proximal end 116 of catheter 110 to data acquisition device 140.

Note that in some embodiments of system 100, multiplexer 146 is not employed for various reasons, such as sufficient electrical conductors being provided in catheter 110 for all electrode channels, or other hardware design considerations. In other embodiments, multiplexer 146 is incorporated into catheter 110 or into data acquisition device 140. In still further embodiments, multiplexer 146 is optional or not provided at all, and data acquisition device 140, ablation module 150, and/or pacing module 160 are employed separately and/or operate independently from one another. In addition, in some embodiments computing device 300 may be combined or integrated with one or more of data acquisition device 140, ablation module 150, and/or pacing module 160.

In one embodiment, a medical practitioner or health care professional employs catheter 110 as a roving catheter to locate the site of the location of the source of a cardiac rhythm disorder or irregularity in the endocardium quickly and accurately, without the need for open-chest and open-heart surgery. In one embodiment, this is accomplished by using multi-electrode catheter 110 in combination with real-time or near-real-time data processing and interactive display by computer 300, and optionally in combination with imaging and/or navigation system 70. In one embodiment, multi-electrode catheter 110 deploys at least a two-dimensional array of electrodes against a site of the endocardium at a location that is to be mapped, such as through the use of a Biosense Webster® PENTARAY® EP mapping catheter. The intracardiac or electrogram signals detected by the catheter's electrodes provide data sampling of the electrical activity in the local site spanned by the array of electrodes.

In one embodiment, the electrogram signal data are processed by computer 300 to produce a display showing the locations(s) of the source(s) of cardiac rhythm disorders and/or irregularities in the patient's heart 10 in real-time or near-real-time, further details of which are provided below. That is, at and between the sampled locations of the patient's endocardium, computer 300 may be configured to compute and display in real-time or near-real-time an estimated, detected and/or determined location(s) of the site(s), source (s) or origin)s) of the cardiac rhythm disorder(s) and/or irregularity(s) within the patient's heart 10. This permits a medical practitioner to move interactively and quickly the electrodes of catheter 110 towards the location of the source of the cardiac rhythm disorder or irregularity.

In some embodiments of system 100, one or more electrodes, sensors or probes detect cardiac activation from the surface of the patient's body as surface ECGs, or remotely without contacting the patient's body (e.g., using magneto-cardiograms). In another example, some electrodes, sensors or probes may derive cardiac activation information from echocardiograms. In various embodiments of system 100, external or surface electrodes, sensors and/or probes can be used separately or in different combinations, and further may also be used in combination with intracardiac electrodes, sensors and/or probes inserted within the patient's heart 10. Many different permutations and combinations of the various components of system 100 are contemplated having, for example, reduced, additional or different numbers of electrical sensing and other types of electrodes, sensors and/or transducers.

Continuing to refer to FIG. 1(a), EP mapping system or data acquisition device 140 is configured to condition the analog electrogram signals delivered by catheter 110 from electrodes A1 through H8 in amplifier 142. Conditioning of the analog electrogram signals received by amplifier 142 may include, but is not limited to, low-pass filtering, high-pass filtering, bandpass filtering, and notch filtering. The conditioned analog signals are then digitized in analog-to-digital converter (ADC) 144. ADC 144 may further include a digital signal processor (DSP) or other type of processor which is configure to further process the digitized electrogram signals (e.g., low-pass filter, high-pass filter, bandpass filter, notch filter, automatic gain control, amplitude adjustment or normalization, artifact removal, etc.) before they are transferred to computer or computing device 300 for further processing and analysis.

As discussed above, in some embodiments, multiplexer 146 is separate from catheter 110 and data acquisition device 140, and in other embodiments multiplexer 146 is combined in catheter 110 or data acquisition device 140.

In some embodiments, the rate at which individual electrogram and/or ECG signals are sampled and acquired by system 100 can range between about 0.25 milliseconds and about 8 milliseconds, and may be about 0.5 milliseconds, about 1 millisecond, about 2 milliseconds or about 4 milliseconds. Other sample rates are also contemplated. While in some embodiments system 100 is configured to provide unipolar signals, in other embodiments system 100 is configured to provide bipolar signals.

In one embodiment, system 100 can include a BARD® LABSYSTEM™ PRO EP Recording System, which is a computer and software driven data acquisition and analysis tool designed to facilitate the gathering, display, analysis, pacing, mapping, and storage of intracardiac EP data. Also in one embodiment, data acquisition device 140 can include a BARD® CLEARSIGN™ amplifier, which is configured to amplify and condition electrocardiographic signals of biologic origin and pressure transducer input, and transmit such information to a host computer (e.g., computer 300 or another computer).

As shown in FIG. 1(a), and as described above, in some embodiments system 100 includes ablation module 150, which may be configured to deliver RF ablation energy through catheter 110 and corresponding ablation electrodes disposed near distal end 112 thereof, and/or to deliver RF ablation energy through a different catheter (not shown in FIG. 1(a)). Suitable ablation systems and devices include, but are not limited to, cryogenic ablation devices and/or systems, radiofrequency ablation devices and/or systems, ultrasound ablation devices and/or systems, high-intensity focused ultrasound (HIFU) devices and/or systems, chemical ablation devices and/or systems, and laser ablation devices and/or systems.

When system 100 is operating in an optional ablation mode, multi-electrode catheter 110 fitted with ablation electrodes, or a separate ablation catheter, is energized by ablation module 150 under the control of computer 300, control interface 170, and/or another control device or module. For example, an operator may issue a command to ablation module 150 through input device 320 to computer 300. In one embodiment, computer 300 or another device controls ablation module 150 through control interface 170. Control of ablation module 150 can initiate the delivery of a programmed series of electrical energy pulses to the endocardium via catheter 110 (or a separate ablation catheter, not shown in FIG. 1(a)). One embodiment of an ablation method and device is disclosed in U.S. Pat. No. 5,383,917 to Desai et al., the entirety of which is hereby incorporated by reference herein.

In an alternative embodiment, ablation module 150 is not controlled by computer 300, and is operated manually directly under operator control. Similarly, pacing module 160 may also be operated manually directly under operator control. The connections of the various components of system 100 to catheter 110, to auxiliary catheters, or to surface electrodes may also be switched manually or using multiplexer 146 or another device or module.

When system 100 is operating in an optional pacing mode, multi-electrode catheter 110 is energized by pacing module 160 operating under the control of computer 300 or another control device or module. For example, an operator may issue a command through input device 320 such that computer 300 controls pacing module 160 through control interface 170, and multiplexer 146 initiates the delivery of a programmed series of electrical simulating pulses to the endocardium via the catheter 110 or another auxiliary catheter (not shown in FIG. 1(a)). One embodiment of a pacing module is disclosed in M. E. Josephson et al., in "VENTRICULAR ENDOCARDIAL PACING II, The Role of Pace Mapping to Localize Origin of Ventricular Tachycardia," The American Journal of Cardiology, vol. 50, November 1982.

Computing device or computer 300 is appropriately configured and programmed to receive or access the electrogram signals provided by data acquisition device 140. Computer 300 is further configured to analyze or process such electrogram signals in accordance with the methods, functions and logic disclosed and described herein so as to permit reconstruction of cardiac activation information from the electrogram signals. This, in turn, makes it possible to locate with at least some reasonable degree of precision the location of the source of a heart rhythm disorder or irregularity. Once such a location has been discovered, the source may be eliminated or treated by means that include, but are not limited to, cardiac ablation.

In one embodiment, and as shown in FIG. 1(a), system 100 also comprises a physical imaging and/or navigation system 70. Physical imaging and/or navigation device 60 included in system 70 may be, by way of example, a 2- or 3-axis fluoroscope system, an ultrasonic system, a magnetic resonance imaging (MRI) system, a computed tomography (CT) imaging system, and/or an electrical impedance tomography EIT) system. Operation of system 70 be controlled by computer 300 via control interface 170, or by other control means incorporated into or operably connected to imaging or navigation system 70. In one embodiment, computer 300 or another computer triggers physical imaging or navigation system 60 to take "snap-shot" pictures of the heart 10 of a patient (body not shown). A picture image is detected by a detector 62 along each axis of imaging, and can include a silhouette of the heart as well as a display of the inserted catheter 110 and its electrodes A1-H8 (more about which is said below), which is displayed on imaging or navigation display 64. Digitized image or navigation data may be provided to computer 300 for processing and integration into computer graphics that are subsequently displayed on monitor or display 64 and/or 324.

In one embodiment, system 100 further comprises or operates in conjunction with catheter or electrode position transmitting and/or receiving coils or antennas located at or near the distal end of an EP mapping catheter 110, or that of an ablation or navigation catheter 110, which are configured to transmit electromagnetic signals for intra-body navigational and positional purposes.

In one embodiment, imaging or navigation system 70 is used to help identify and determine the precise two- or three-dimensional positions of the various electrodes included in catheter 110 within patient's heart 10, and is configured to provide electrode position data to computer 300. Electrodes, position markers, and/or radio-opaque markers can be located on various portions of catheter 110, mapping electrode assembly 120 and/or distal end 112, or can be configured to act as fiducial markers for imaging or navigation system 70.

Medical navigation systems suitable for use in the various embodiments described and disclosed herein include, but are not limited to, image-based navigation systems, model-based navigation systems, optical navigation systems, electromagnetic navigation systems (e.g., BIOSENSE® WEBSTER® CARTO® system), and impedance-based navigation systems (e.g., the St. Jude® ENSITE™ VELOCITY™ cardiac mapping system), and systems that combine attributes from different types of imaging AND navigation systems and devices to provide navigation within the human body (e.g., the MEDTRONIC® STEALTHSTATION® system).

In view of the structural and functional descriptions provided herein, those skilled in the art will appreciate that portions of the described devices and methods may be configured as processes, methods, data processing systems, and/or computer methods. Accordingly, these portions of the devices and methods described herein may take the form of a hardware embodiment, a software embodiment, or an embodiment combining software and hardware, such as shown and described with respect to computer system 300 illustrated in FIG. 1(b). Furthermore, portions of the devices and methods described herein may be a process or method stored in a computer-usable storage medium having computer readable program code on the medium. Any suitable computer-readable medium may be utilized including, but not limited to, static and dynamic storage devices, hard disks, optical storage devices, and magnetic storage devices.

Certain embodiments of portions of the devices and methods described herein are also described with reference to block diagrams of methods, processes, and systems. It will be understood that such block diagrams, and combinations of blocks diagrams in the Figures, can be implemented using computer-executable instructions. These computer-executable instructions may be provided to one or more processors of a general purpose computer, a special purpose computer, or any other suitable programmable data processing apparatus (or a combination of devices and circuits) to produce a machine, such that the instructions, which executed via the processor(s), implement the functions specified in the block or blocks of the block diagrams.

These computer-executable instructions may also be stored in a computer-readable memory that can direct computer 300 or other programmable data processing apparatus to function in a particular manner, such that the instructions stored in the computer-readable memory result in an article of manufacture including instructions which implement the function specified in an individual block, plurality of blocks, or block diagram. The computer program instructions may also be loaded onto computer 300 or other programmable data processing apparatus to cause a series of operational steps to be performed on the computer or other programmable apparatus to produce a computer implemented process such that the instructions which execute on computer 300 or other programmable apparatus provide steps for implementing the functions specified in the an individual block, plurality of blocks, or block diagram.

Figure 1B:
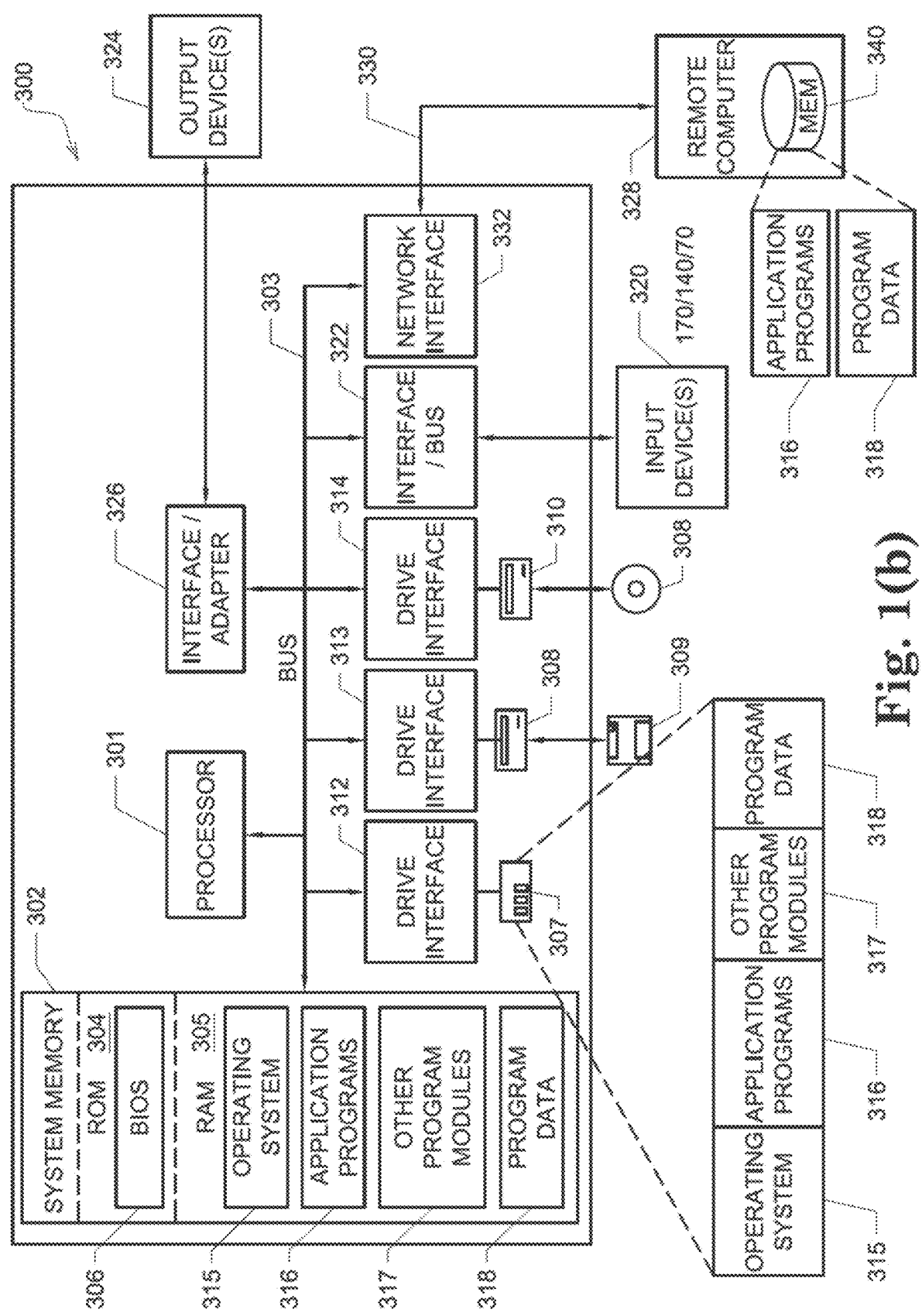
FIG. 1(b) shows one embodiment of a computer system 300.

In this regard, FIG. 1(b) illustrates only one example of a computer system 300 (which, by way of example, can include multiple computers or computer workstations) that can be employed to execute one or more embodiments of the devices and methods described and disclosed herein, such as devices and methods configured to acquire and process sensor or electrode data, to process image data, and/or transform sensor or electrode data and image data associated with the analysis of cardiac electrical activity and the carrying out of the combined electrophysiological mapping and analysis of the patient's heart 10 and ablation therapy delivered thereto.

Computer system 300 can be implemented on one or more general purpose computer systems or networked computer systems, embedded computer systems, routers, switches, server devices, client devices, various intermediate devices/nodes or standalone computer systems. Additionally, computer system 300 or portions thereof may be implemented on various mobile devices such as, for example, a personal digital assistant (PDA), a laptop computer and the like, provided the mobile device includes sufficient processing capabilities to perform the required functionality.

In one embodiment, computer system 300 includes processing unit 301 (which may comprise a CPU, controller, microcontroller, processor, microprocessor or any other suitable processing device), system memory 302, and system bus 303 that operably connects various system components, including the system memory, to processing unit 301. Multiple processors and other multi-processor architectures also can be used to form processing unit 301. System bus 303 can comprise any of several types of suitable bus architectures, including a memory bus or memory controller, a peripheral bus, or a local bus. System memory 302 can include read only memory (ROM) 304 and random access memory (RAM) 305. A basic input/output system (BIOS) 306 can be stored in ROM 304 and contain basic routines configured to transfer information and/or data among the various elements within computer system 300.

Computer system 300 can include a hard disk drive 303, a magnetic disk drive 308 (e.g., to read from or write to removable disk 309), or an optical disk drive 310 (e.g., for reading CD-ROM disk 311 or to read from or write to other optical media). Hard disk drive 303, magnetic disk drive 308, and optical disk drive 310 are connected to system bus 303 by a hard disk drive interface 312, a magnetic disk drive interface 313, and an optical drive interface 314, respectively. The drives and their associated computer-readable media are configured to provide nonvolatile storage of data, data structures, and computer-executable instructions for computer system 300. Although the description of computer-readable media above refers to a hard disk, a removable magnetic disk and a CD, other types of media that are readable by a computer, such as magnetic cassettes, flash memory cards, digital video disks and the like, in a variety of forms, may also be used in the operating environment; further, any such media may contain computer-executable instructions for implementing one or more parts of the devices and methods described and disclosed herein.

A number of program modules may be stored in drives and RAM 303, including operating system 315, one or more application programs 316, other program modules 313, and program data 318. The application programs and program data can include functions and methods programmed to acquire, process and display electrical data from one or more sensors, such as shown and described herein. The application programs and program data can include functions and methods programmed and configured to process data acquired from a patient for assessing heart function and/or for determining parameters for delivering a therapy and/or assessing heart function, such as shown and described herein with respect to FIGS. 1-10(f).

A health care provider or other user may enter commands and information into computer system 300 through one or more input devices 320, such as a pointing device (e.g., a mouse, a touch screen, etc.), a keyboard, a microphone, a joystick, a game pad, a scanner, and the like. For example, the user can employ input device 320 to edit or modify the data being input into a data processing method (e.g., only data corresponding to certain time intervals). These and other input devices 320 may be connected to processing unit 301 through a corresponding input device interface or port 322 that is operably coupled to the system bus, but may be connected by other interfaces or ports, such as a parallel port, a serial port, or a universal serial bus (USB). One or more output devices 324 (e.g., display, a monitor, a printer, a projector, or other type of display device) may also be operably connected to system bus 303 via interface 326, such as through a video adapter.

Computer system 300 may operate in a networked environment employing logical connections to one or more remote computers, such as remote computer 328. Remote computer 328 may be a workstation, a computer system, a router, or a network node, and may include connections to many or all the elements described relative to computer system 300. The logical connections, schematically indicated at 330, can include a local area network (LAN) and/or a wide area network (WAN).

When used in a LAN networking environment, computer system 300 can be connected to a local network through a network interface or adapter 332. When used in a WAN networking environment, computer system 300 may include a modem, or may be connected to a communications server on the LAN. The modem, which may be internal or external, can be connected to system bus 303 via an appropriate port interface. In a networked environment, application programs 316 or program data 318 depicted relative to computer system 300, or portions thereof, may be stored in a remote memory storage device 340.

Figure 2:
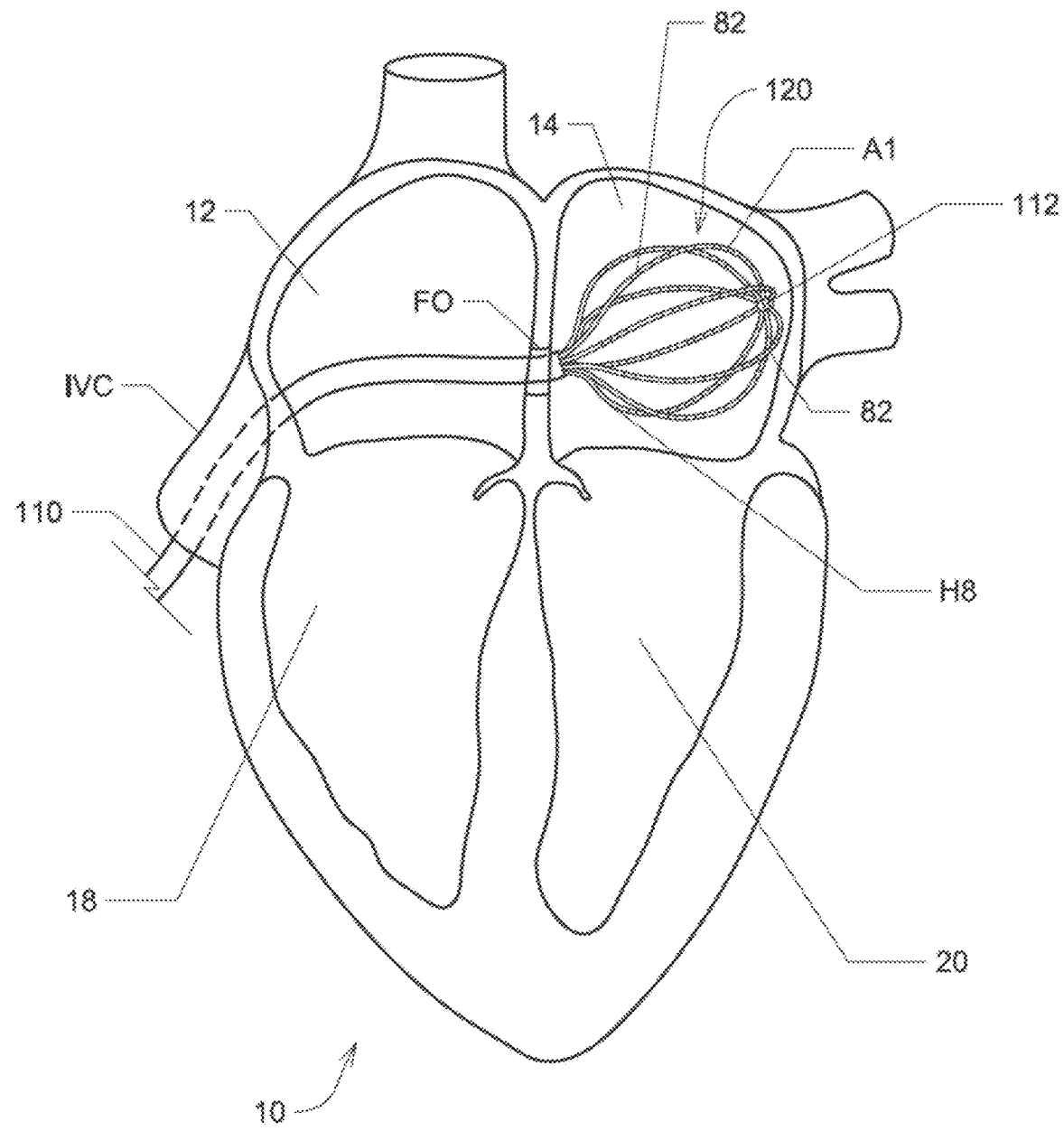
FIG. 2 shows an illustrative view of one embodiment of a distal portion of catheter 110 inside a patient's left atrium 14.

Referring now to FIG. 2, there is shown an illustrative view of one embodiment of a distal portion of catheter 110 inside a patient's left atrium 14. As shown in FIG. 2, heart 10 includes right atrium 12, left atrium 14, right ventricle 18, and left ventricle 20. Mapping electrode assembly 120 is shown in an expanded or open state inside left atrium 13 after it has been inserted through the patient's inferior vena cava and foramen ovalen ("IVC" and "FO" in FIG. 2), and in one embodiment is configured to obtain electrogram signals from left atrium 12 via an 8×8 array of electrodes A1 through H8, which as shown comprises individual electrodes 82. Mapping electrode assembly and catheter 110 may also be positioned within the patient's right atrium 12, left ventricle 18 and right ventricle 20.

Figure 3:
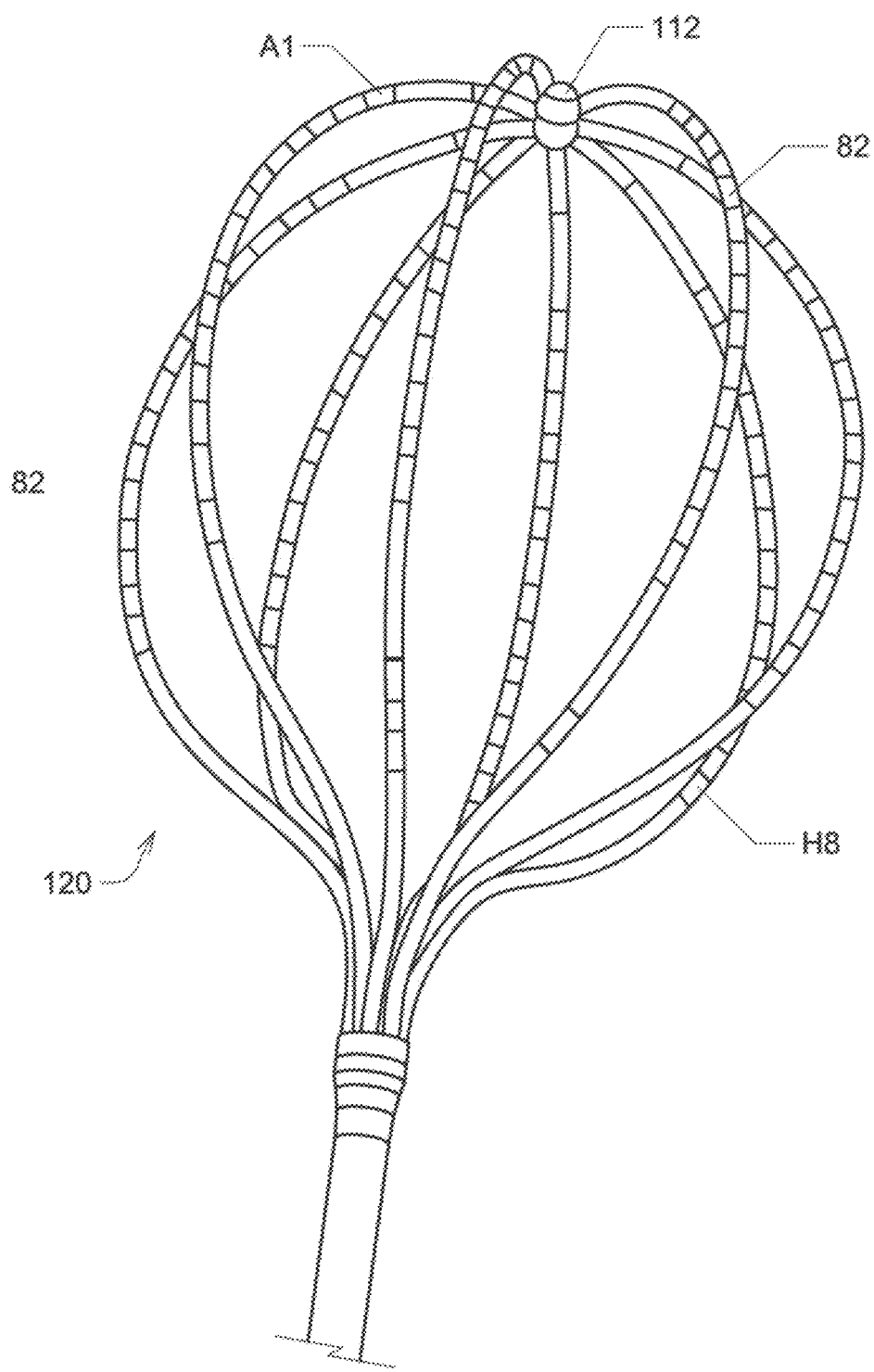
FIG. 3 shows an illustrative embodiment of a mapping electrode assembly 120.

FIG. 3 shows an illustrative embodiment of a mapping electrode assembly 120, which in FIG. 3 forms a distal portion of a Boston Scientific® CONSTELLATION® full contact mapping catheter. The CONSTELLATION EP catheter permits full-contact mapping of a patient's heart chamber, and may also be employed to facilitate the assessment of entrainment, conduction velocity studies, and refractory period in a patient's heart 10. Mapping electrode assembly 120 shown in FIG. 3 permits the simultaneous acquisition of longitudinal and circumferential signals for more accurate 3-D mapping, and features a flexible basket design that conforms to atrial anatomy and aids aid in accurate placement. Sixty-four electrodes A1 through H8 (or individual electrodes 82) can provide comprehensive, real-time 3-D information over a single heartbeat.

Figure 4:
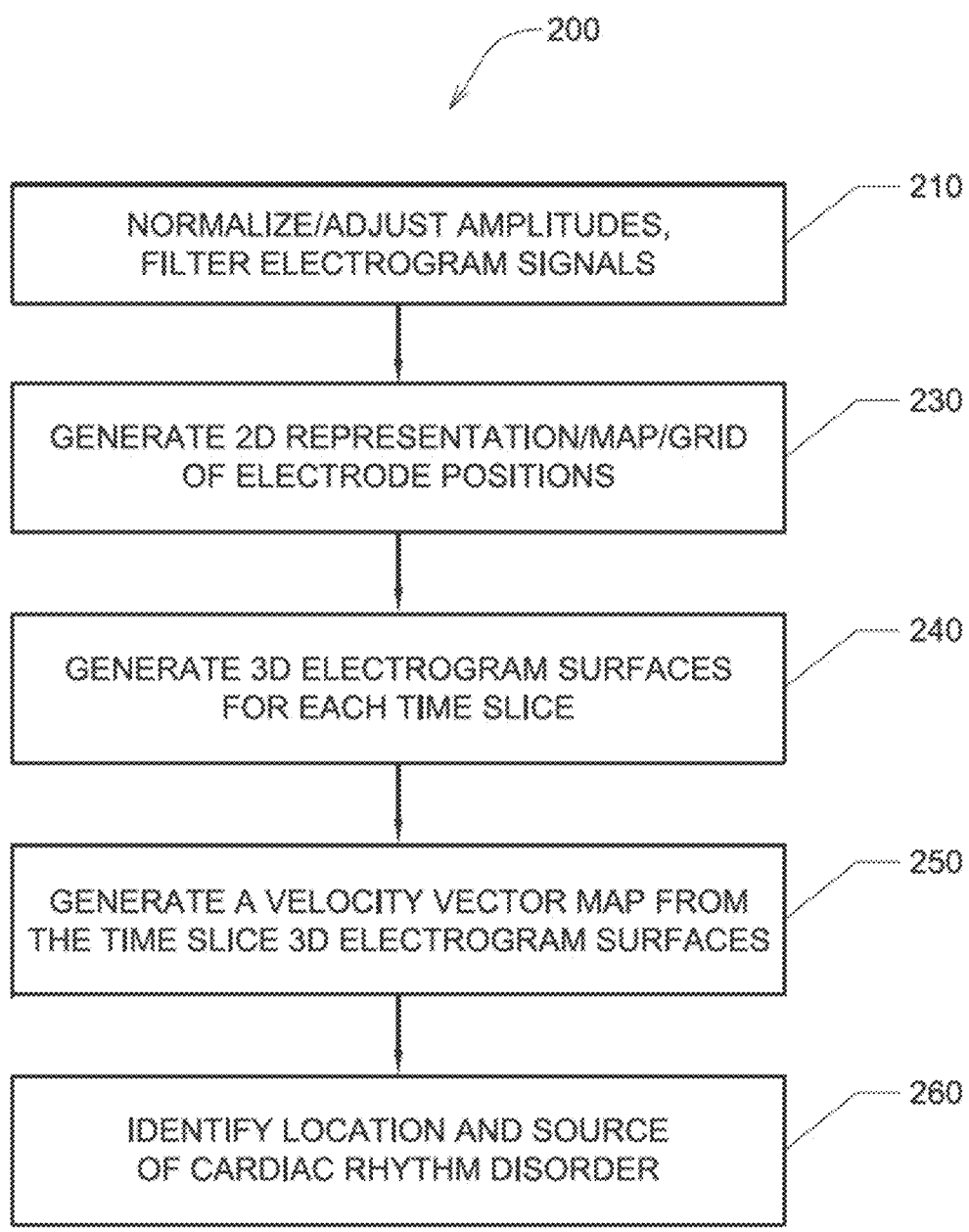
FIG. 4 shows one embodiment of a method 200 of detecting a location of a source of at least one cardiac rhythm disorder in a patient's heart.

FIG. 4 shows one embodiment of a method 200 of detecting a location of a source of at least one cardiac rhythm disorder in a patient's heart. At step 210, the amplitudes of electrogram signals acquired from electrodes located inside a patient's heart are normalized or adjusted. At step 230, positions A1 through H8 corresponding to each of the electrodes of mapping electrode assembly 120 are assigned to the individual electrogram signals that have been acquired. At step 230, a two-dimensional (2D) spatial map of electrode positions A1 through H8 is generated or provided. In some embodiments, a three-dimensional (3D) spatial map of electrode positions A1 through H8 is generated or provided. (As discussed above, fewer or more than 64 electrodes may be used to measure electrogram signals and/or surface ECGs, and electrode arrays other than 8×8 or rectangular grids are contemplated in the various embodiments.)

For discrete or selected times over which the electrogram signals are being analyzed and processed, at step 240 the amplitude-adjusted electrogram signals are processed to generate a plurality of three-dimensional electrogram surfaces (which according to one embodiment may be smoothed electrogram surfaces) corresponding at least partially to the 2D (or 3D) map, one surface being generated for each such discrete time. At step 250, the plurality of three-dimensional electrogram surfaces that have been generated through time are processed to generate a velocity vector map corresponding at least partially to the 2D (or 3D) map, which can also be called a three-dimensional electrographic flow or EGF map. The velocity vector map or EGF map is configured to reveal the location of the source of the at least one cardiac rhythm disorder. In a subsequent optional step (not shown in FIG. 4), method 200 further comprises ablating patient's heart 10 at the location of the source of the cardiac rhythm disorder indicated by the velocity vector map.

Method 200 outlined in FIG. 4 presents one embodiment of a method of processing electrogram signals provided by one or more mapping catheters so as to transform time domain waveform information into space domain information, and then calculate velocity vector maps that correspond to normalized space potential profile movements for each point in space. For reasons that are explained below, method 200 has the advantages that it is robust against artifacts and provides a virtual resolution that is higher than the actual electrode density employed to acquire the EP mapping data through the use of a fitting method that determines the most likely mean spatial velocity map derived from hundreds of individual samples of amplitude patterns recorded by the mapping electrodes.

As described above, in step 210 of FIG. 4 the amplitudes of electrogram signals acquired from electrodes located inside the patient's heart are normalized or otherwise adjusted. In step 240, the amplitude-adjusted electrogram signals are processed across a 2D or 3D map to generate a plurality of three-dimensional electrogram surfaces, one surface being generated for each such discrete time. In one embodiment, the resulting individual time-slice surfaces can be strung together sequentially to provide a time-varying depiction of electrical activation occurring over the portion of the patient's heart that has been monitored. According to embodiments that have been discovered to be particularly efficacious in the field of intracardiac EP monitoring and data processing and analysis, at least portions of the electrogram surfaces are found to correspond to estimated wave shapes, and are generated using Green's function, which in some embodiments, and by way of non-limiting example, may be combined with two- or three-dimensional bi-harmonic spline interpolation functions to generate such surfaces.

In one embodiment, electrogram signal data acquired from the patient's heart 10 are not equidistantly sampled. For example, in one such embodiment, electrogram signal data acquired from the patient's heart 10 are not equidistantly sampled by mapping electrode assembly 120, and instead are assigned their respective chessboard locations A1 through H8 as approximations of electrode locations in a cylindrical 2D projection of a grid representative of the interior surface of the patient's heart that is being mapped. In many applications, it has been discovered that such approximations of electrode locations yield perfectly useable and accurate results when steps 230 through 250 are carried out after steps 210 and 230.

In another embodiment, when superimposing the acquired electrogram signal data onto a 2D or 3D map or grid in step 230, the electrogram signal data may be associated with their actual or more accurately estimated positions in the 2D projection of the grid using positional data provided by, for example, imaging or navigation system 70. Resampling of electrogram signals on the grid may also be carried out. Gridding may also be carried out such as by convolution-type filtering, Kriging, and using splines. Most gridding techniques operate on an equidistant grid and solve the equations governing the gridding process with either finite difference or finite element implementations.

One approach that has been discovered to work particularly well with electrogram signal data is to determine the Green's function associated with each electrogram value assigned to a given chessboard location, and then construct the solution as a sum of contributions from each data point, weighted by the Green's function evaluated for each point of separation. Biharmonic spline interpolation, which as described above may be employed in conjunction with Green's function, has also been discovered to work especially well in the context of processing and analyzing electrogram signal data. In some embodiments, undesirable oscillations between data points are removed by interpolation with splines in tension, also using Green's function. A Green's function technique for interpolation and surface fitting and generation of electrogram signal data has been found to be superior to conventional finite-difference methods because, among other things, the model can be evaluated at arbitrary x,y locations rather than only on a rectangular grid. This is a very important advantage of using Green's function in step 240, because precise evenly-spaced-apart grid locations, resampling of electrogram signals, and finite-difference gridding calculations are not required to generate accurate representations of electrogram surfaces in step 240.

In one embodiment, Green's function $G(x; x')$ is employed in step 240 for a chosen spline and geometry to interpolate data at regular or arbitrary output locations. Mathematically, the solution is $w(x) = \text{sum } \{c(i) \, G(x'; x(i))\}$, for $i=1, n$, and a number of data points $\{x(i), w(i)\}$. Once the n coefficients $c(i)$ have been calculated, the sum may be evaluated at any output point x. A selection is made between minimum curvature, regularized, or continuous curvature splines in tension for either 1-D, 2-D, or 3-D Cartesian coordinates or spherical surface coordinates. After removing a linear or planar trend (i.e., in Cartesian geometries) or mean values (i.e., spherical surfaces) and normalizing residuals, a least-squares matrix solution for spline coefficients $c(i)$ may be determined by solving the n by n linear system $w(j) = \text{sum-over-}i \{c(i) \, G(x(j); x(i))\}$, for $j=1, n$; this solution yields an exact interpolation of the supplied data points. For further details regarding the methods and mathematics underlying Green's function, see, for example: (1) "Moving Surface Spline Interpolation Based on Green's Function," Xingsheng Deng and Zhong-an Tang, Math. Geosci (2011), 43:663-680 ("the Deng paper"), and (2) "Interpolation with Splines in Tension: A Green's Function Approach," Paul Wessel and David Bercovici, Mathematical Geology, 77-93, Vol. 30, No. 1, 1998 ("the Wessel paper"). The respective entireties of the Deng and Wessel papers are hereby incorporated by reference herein.

Still further details regarding the use of Green's function in interpolating and generating surfaces may be found in: Interpolation by regularized spline with tension: I. Theory and implementation, Mitasova, H., and L. Mitas, 1993, Math. Geol., 25, 641-655; Parker, R. L., 1994, Geophysical Inverse Theory, 386 pp., Princeton Univ. Press, Princeton, N.J.; Sandwell, D. T., 1987, Biharmonic spline interpolation of Geos-3 and Seasat altimeter data, Geophys. Res. Lett., 14, 139-142; Wessel, P., and J. M. Becker, 2008, Interpolation using a generalized Green's function for a spherical surface spline in tension, Geophys. J. Int, 174, 21-28, and Wessel, P., 2009, A general-purpose Green's function interpolator, Computers & Geosciences, 35, 1247-1254. Moving Surface Spline Interpolation Based on Green's Function, Xingsheng Deng, Zhong-an Tang, Mathematical Geosciences, August 2011, Volume 43, Issue 6, pp 663-680.

Note, however, that a number of different surface smoothing, surface fitting, surface estimation and/or surface/data interpolation processing techniques may be employed in step 240 of FIG. 4, which are not limited to Green's function, or use in conjunction with Green's function, and which include, but are not limited to, inverse distance weighted methods of interpolation, triangulation with linear interpolation, bilinear surface interpolation methods, bivariate surface interpolation methods, cubic convolution interpolation methods, Kriging interpolation methods, Natural Neighbor or "area-stealing" interpolation methods, spline interpolation techniques (including bi-harmonic spline fitting techniques and "spline with barriers" surface interpolation methods), global polynomial interpolation methods, moving least squares interpolation methods, polynomial least square fitting interpolation methods, simple weighted-average operator interpolation methods, multi-quadric biharmonic function interpolation methods, and artificial neural network interpolation methods. See, for example: "A brief description of natural neighbor interpolation (Chapter 2)," in V. Barnett. Interpreting Multivariate Data. Chichester: John Wiley. pp. 21-36.), and "Surfaces generated by Moving Least Squares Methods," P. Lancaster et al., Mathematics of Computation, Vol. 37, No. 155 (July, 1981), 141-158).

As described above, in step 250 of FIG. 4, the plurality of three-dimensional electrogram surfaces may be processed through time to generate a velocity vector map or EGF map corresponding at least partially to the 2D (or 3D) map, the velocity vector map being configured to reveal the location of the source of the at least one cardiac rhythm disorder. According to embodiments that have been discovered to be particularly efficacious in the field of intracardiac EP monitoring and subsequent data processing and analysis, at least portions of the velocity vector map are generated using one or more optical flow analysis and estimation techniques and methods. Such optical flow analysis techniques may include one or more of Horn-Schunck, Buxton-Buston, Black-Jepson, phase correlation, block-based, discrete optimization, Lucas-Kanade, and differential methods of estimating optical flow. From among these various optical flow estimation and analysis techniques and methods, however, the Horn-Schunck method has so far been discovered to provide superior results in the context of processing and analyzing cardiac electrogram signals, for reasons that are discussed in further detail below.

Further details and information regarding EGF techniques are to be found in U.S. Pat. No. 10,201,277 to Ruppersberg entitled "Systems, Devices, Components and Methods for Detecting the Locations of Sources of Cardiac Rhythm Disorders in a Patient's Heart" ("the '277 patent") and U.S. Pat. No. 10,143,374 to Ruppersberg, also entitled "Systems, Devices, Components and Methods for Detecting the Locations of Sources of Cardiac Rhythm Disorders in a Patient's Heart" ("the '374 patent"). The respective entireties of the '277 and '374 patents are hereby incorporated by reference herein.

Figure 5:
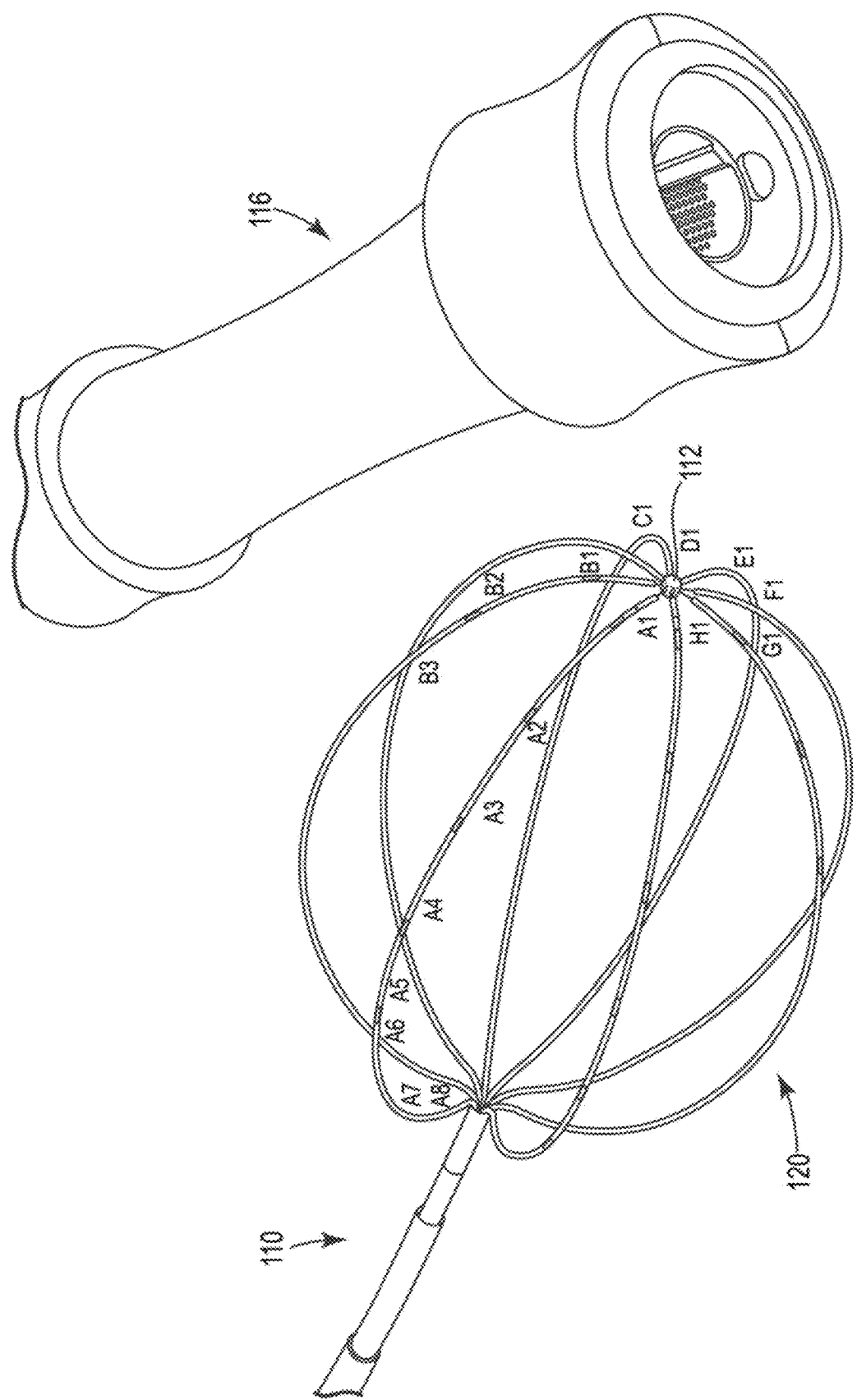
FIG. 5 shows one embodiment of a basket catheter 110.

Referring now to FIG. 5, there is shown one embodiment of a basket catheter 110 comprising mapping electrode assembly 120 (which in the illustrated embodiment comprises electrodes A1 through H8), distal end 112, and proximal end and handle 116 (with output pins, as shown). The winding direction of the mapping electrode assembly 120 is clockwise, looking from the distal end (1) towards the proximal end (8). Electrographic flow (EGF) mapping, discussed in detail above, is used to map electrical activity inside human heart 10. In one embodiment, basket catheter 110 is introduced through a patient's groin, up along the inferior vena cava (IVC) into the right atrium (RA). To map the left atrium (LA), a small 1 mm diameter hole is made in the septum wall using a needle, through which the basket or mapping electrode assembly 120 is introduced into the LA. Once the basket is in place, each of the 64 electrodes on the basket (8 splines, each having 8 electrodes) samples local electrical activity at 1 kHz. This activity is given a 24-bit value representing relative voltage difference (±150 mV) to a ground electrode, which is usually located on the left leg or lower abdomen. We can think of this data as series of images where rows represent splines A through H, and columns represent electrodes 1 through 8:

| A1 | A2 | A3 | ... | A8 |
|----|----|----|-----|----|
| B1 | B2 | B3 | ... | B8 |
| C1 | C2 | C3 | ... | C8 |
| .  | .  | .  | ... | .  |
| H1 | H2 | H3 | ... | H8 |

Implementation Overview—Using WebGL and ThreeJS

In one embodiment, an important implementation requirement for visualization of EGF flow is the capability to run programs in a browser, such as Google Chrome. This requirement directly implies that WebGL (Web Graphics Library) must be used. WebGL, is a low level JavaScript API that closely resembles OpenGL's API. It allows developers to run almost arbitrary commands on the client's GPU in order to render 3D graphics, but also permits the use of some general purpose graphics programming (GPGPU) as well by using textures and pixel shaders. To simplify working with WebGL's low level API, a number of open source projects were founded. The most notable of these are ThreeJS (mrdoob et al.) and BabylonJS. In one embodiment, ThreeJS is employed.

Typescript

JavaScript is not a strongly typed language. This makes it hard to discern which objects have which data associated with them. This is especially true for medium to large graphics programs, since they heavily rely on state. To help solve with this problem, Microsoft developed TypeScript. TypeScript is a language and superset of JavaScript that aims to decorate JavaScript with types. It is also a transpiled language, which means that there is a transpiling step which takes TypeScript source code and turns it into plain (human-readable) JavaScript. In the following example, there is shown TypeScript code and a JavaScript equivalent (which is also valid TypeScript code):

```
Listing: TypeScript example
//TypeScript
function      example(a:number,b:
Vector3): Vector3{returnb.addSca
lar(a)
}
//plainJavaScript
function    example(a,b){
returnb.addScalar(a)
}
```

The main difference between these two code examples is that in the former we know exactly which types are being employed in the function. The editor can help us in this case and provides helpful hints about what is available for parameter b: Vector3.

Python and Bokeh Plotting Library

For many years now, Python has been the leading language for professional data scientists. It has a multitude of libraries for managing and visualizing data. Most notable libraries for interactive plotting on the Web are Bokeh and Plotly's Dash. Both frameworks are good choices, but in some embodiment the context in which a visualization is employed requires Bokeh bindings. Bokeh comes with dozens of different plot types, layouting API, and data streaming capabilities. One of the most important features is extending Bokeh through custom models1, allowing for integration with existing third-party libraries, such as ThreeJS. The developed library can also be used without Bokeh (using plain JavaScript/TypeScript).

Dat.GUI Library

One of the most important features of this library is the ability to change visualization parameters without having to re-render the whole plot. Using dat.GUI2 JavaScript library simplifies this process significantly.

Jupyter Notebook Setup

In some embodiments, flow visualization libraries employ Python version 3.5+. Then Bokeh and Jupyter should be installed using the following commands:
pip install bokeh
pip install jupyter
In some embodiments, features are available only through a JavaScript/TypeScript interface, such as specifying 3D electrode positions.

Using Libraries

In some embodiments, libraries can be configured so they are easy to use. For example, everything a user requires can be placed in the following classes or sub-libraries:
Particle2DModel
Particle3DModel
LIC2DModel
LIC3DModel
In a flow_test_noise.ipynb, a Python usage example is given, with an important part of the code being:

```
from flowvis import Particle3DMod
el
...
```

```
model=Particle3DModel(
...
width=700,height=700,
source=flow_field_source,f
low='flows',
color_map='Inferno8'
...
)
```

Figure 6:
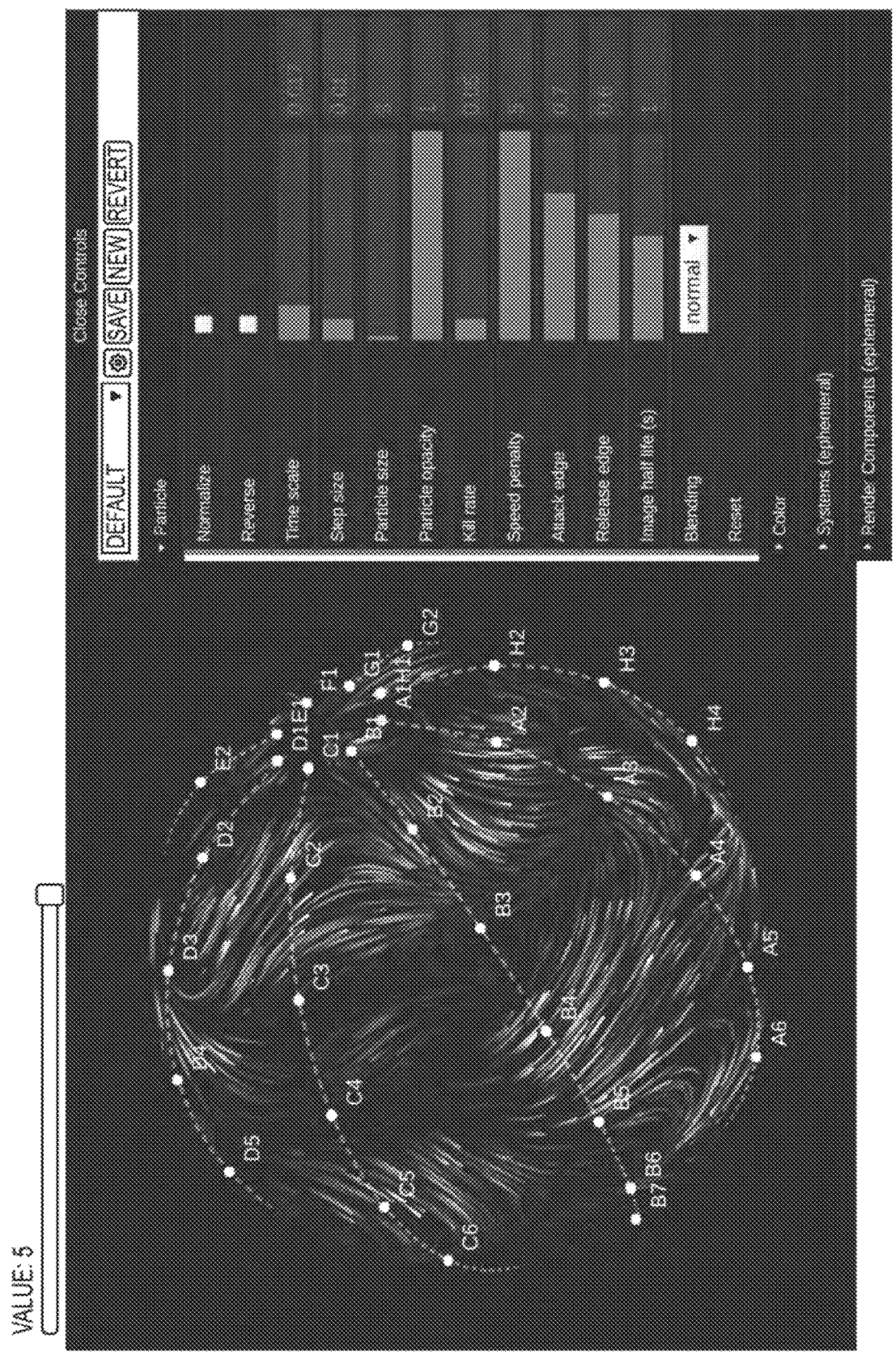
FIG. 6 shows one example of a notebook visualization embodiment.
Figure 7:
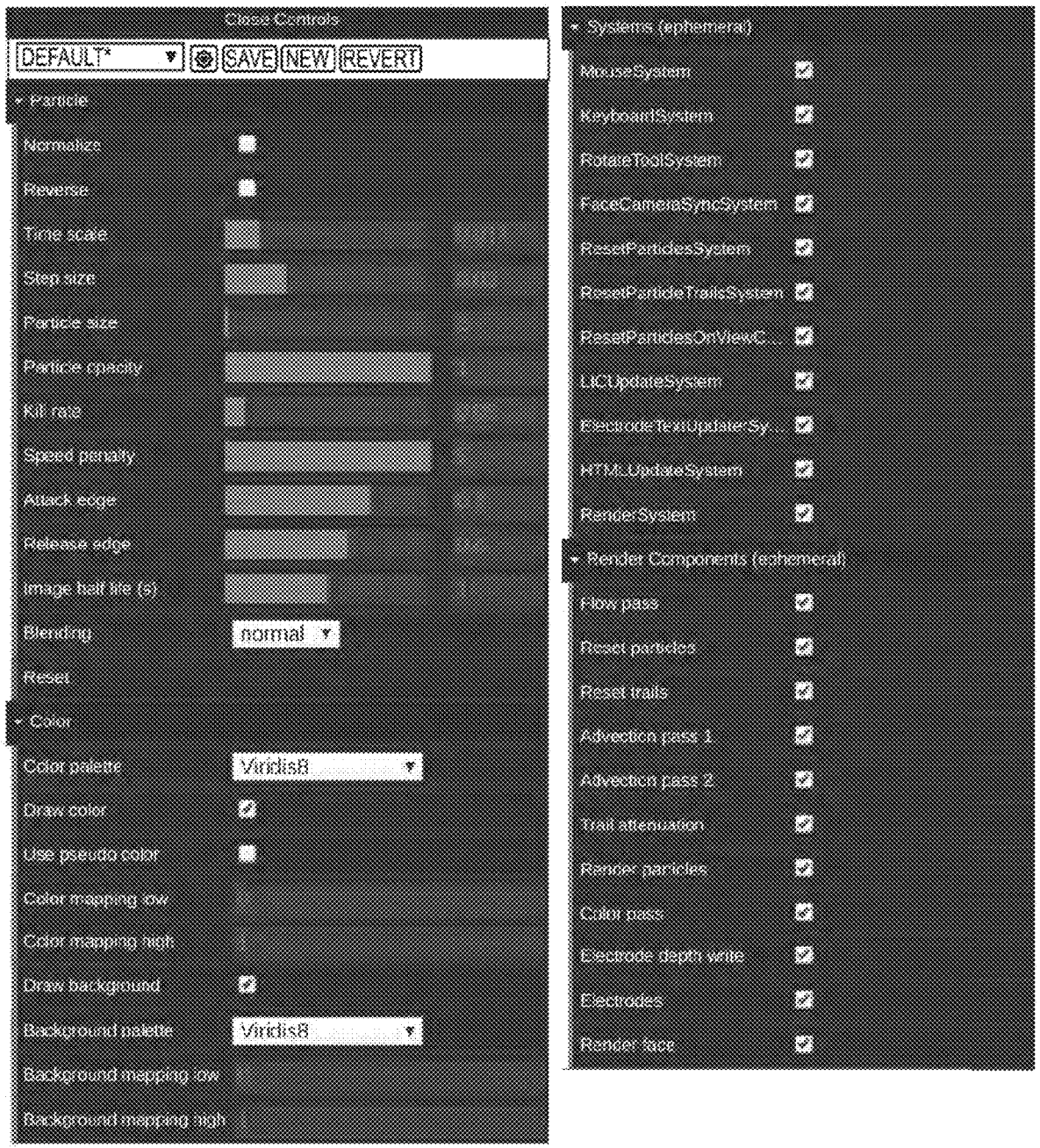
FIG. 7 shows one embodiment of a fully expanded parameter graphical user interface (GUI)

FIG. 6 shows one example of a notebook visualization embodiment generated using Particle3DModel and noise data. At the top of FIG. 6, a slider is shown. The slider is used when there are multiple flow maps to be shown, so the user can flip through them without having to re-render the visualization. On the right, a dat.GUI parameter interface is shown where the user can experiment with different values in real time. This has been discovered to be very important when searching for optimal values, since in some embodiments only a small subset of combinations produces good results. FIG. 7 shows one embodiment of a fully expanded parameter graphical user interface (GUI). Systems contains all systems which can be enabled and/or disabled by a user, and RenderComponents contains all components related to rendering which can be enabled and/or disabled by a user.

METHODS

Quiver Plot

Figure 8A:
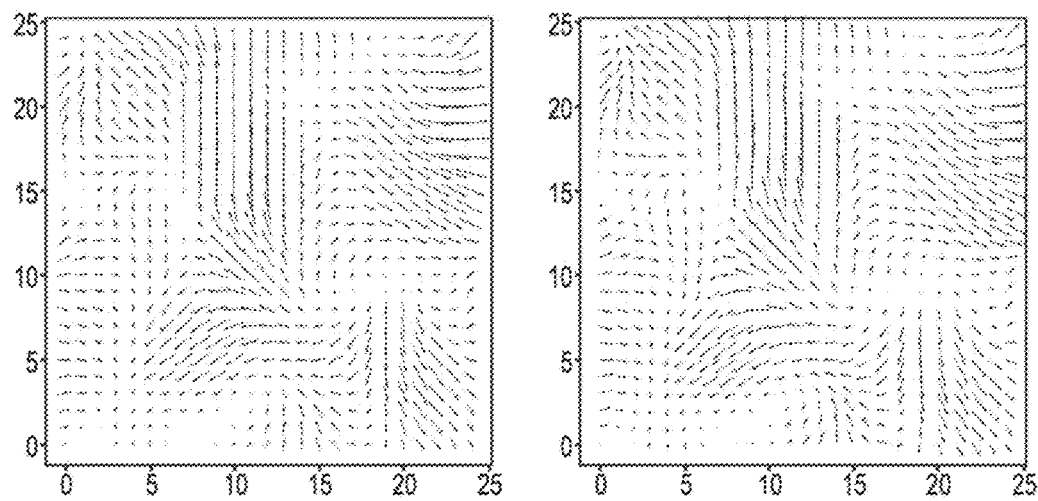
FIGS. 8(a) through 8(c) show embodiments of quiver flow field plots.
Figure 8B:
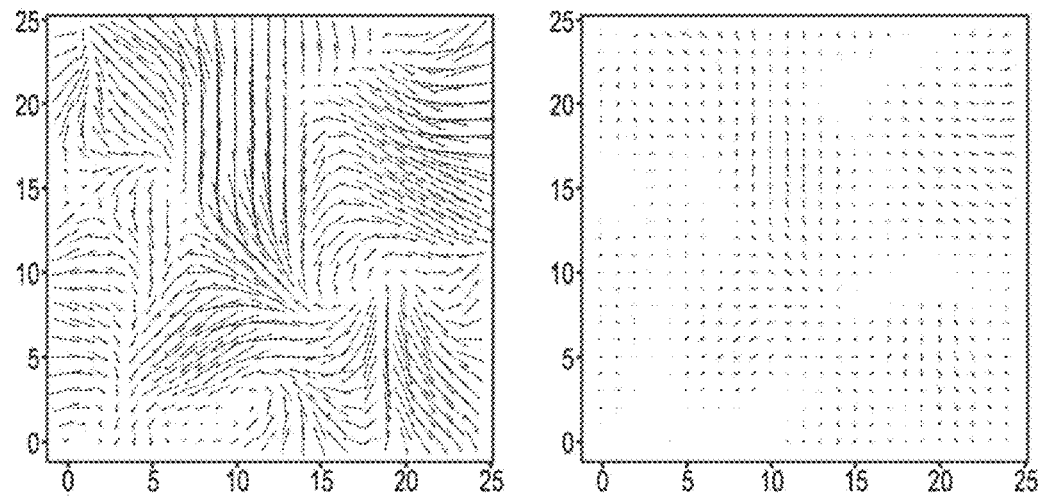
Figure 8C:
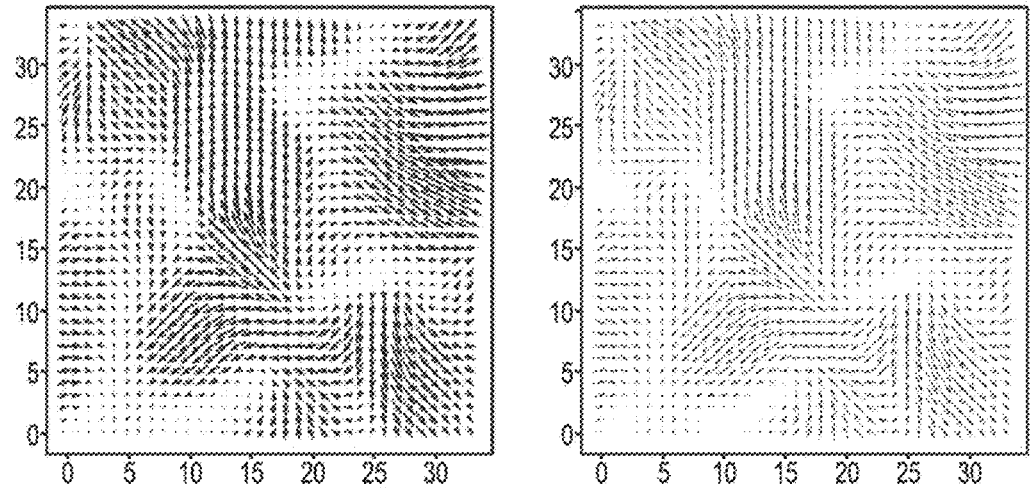

An uncomplicated way to visualize a flow field is to draw arrows representing individual vectors of which the flow field is comprised. We call this a quiver plot. It is a widely recognized visualization method and implemented in many plotting libraries. In FIGS. 8(a) through 8(c) there are shown different embodiments of quiver flow field plots, which illustrate how different parameters can influence the legibility or visual usefulness of a quiver plot to a user.

FIG. 8(a) shows Matplotlib quiver plots with arrows anchored using their midpoints (left figure) and tails (right figure). Midpoint anchors usually yield a better representation of a flow field since they do not shift the image.

FIG. 8(b) shows Matplotlib quiver plots with long arrows (left figure) and short arrows (right figure). Arrow length can be an important parameter in flow filed visualizations. If there is a great deal of variability in flow magnitude, some sort of vector compression must generally be employed. Otherwise, short arrows become too short and long arrows conflict with one another.

FIG. 8(c) shows Matplotlib quiver plots with thick arrows (left figure) and thin arrows (right figure). Thin arrows are generally better suited for representing dense flow fields.

Streamline Plot

Another way to display a flow field, implemented in many plotting libraries, is to use a streamline plot. To understand the streamline plot, we first need to define what a streamline is: a family of curves that are instantaneously tangent to a given flow field. Or, explained more visually, the paths of "massless" particles traveling through a given flow field frozen in time. (If the flow field is time-varying, then other types of curves need to be considered.) A streamline plot visualization method can be derived as follows. First, we define a set of starting points. Then, each point x is advected along the flow field u(x) by a small dt leaving a trail:

$$\frac{d\vec{x}}{dt} = \vec{u}(\vec{x})$$

Figure 9:
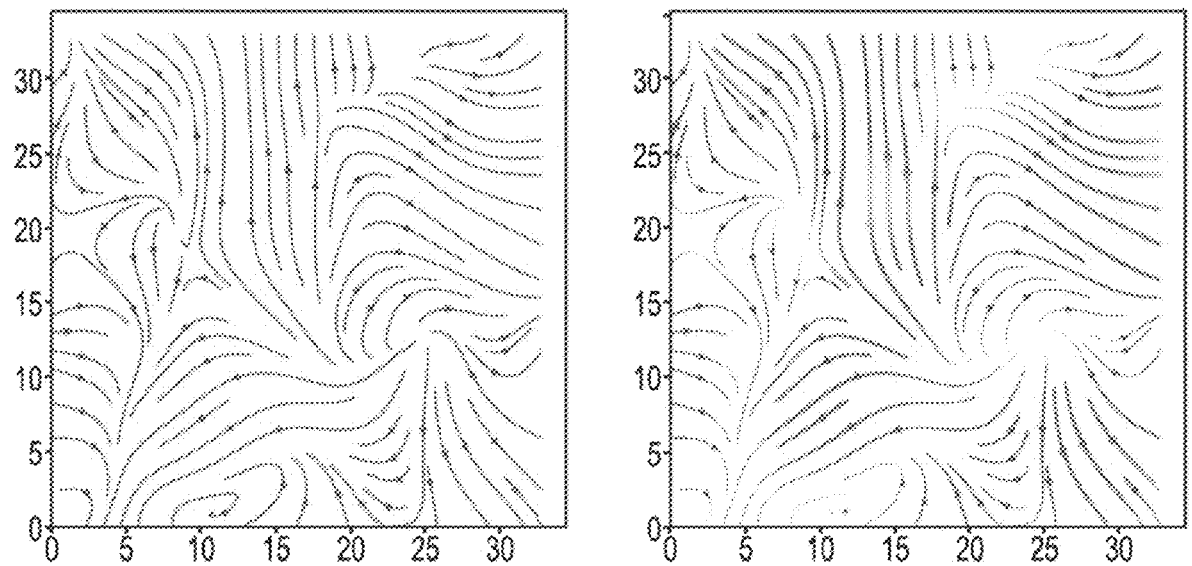
FIG. 9 shows various embodiments of streamline plots.

When two trails get too close to each other, one trail can be terminated so that the density of the flow filed remains relatively constant. Trail density can be a problem, which may be solved by trying out a large number of different starting conditions until a selected scoring function is satisfied. Since we are interested only in relatively snort streamlines, and because flow field generally do not change abruptly, good results can often be achieved using a simple Euler's integration technique. For even better approximation in more dynamic fields and where longer streamlines are present, we can use more complex integration methods like the Midpoint method or Runge-Kutta Matplotlib's streamline plot. FIG. 9 shows a basic streamline plot (left figure) and a varying thickness and color streamline plot (right figure). (To show magnitude, a streamline plot can employ thickness and color.)

Particle Plots

Streamline plots suffer from the same issue as quiver plots: information density often overwhelms such plot types. Ideally, we would like to show lots of short streamlines and animate them, so that areas that are potentially missed in one configuration become visible in another.

A "particle" plot, is exactly that: thousands of particles moving along the flow field on a canvas, leaving a trail that slowly disappears. Since the particles tend to end up in sinks or valleys, a mechanism to reset the particles can be employed, keeping density issues at bay. In one embodiment, a way to make some parts of the flow field more or less populated, depending on a probability mask, can be employed. For example, particles tend to "run away" from sources, so setting high spawn probabilities around such particles can be desirable. A single particle can be represented by 3 numbers: x (horizontal coordinate), y (vertical coordinate) and t ("life" of the particle starting at 1). Particles themselves can be stored in particle target 1 (size N×1, where N is the number of particles) as texels. See FIG. 10(a), where one embodiment of a 2D particle algorithm is illustrated. A 3D version of a particle algorithm differs only in the flow field projection step. FIG. 10(b) shows a particle opacity attack/decay curve, where Life goes from 1.0 to 0.0, and where in each frame two consecutive advection passes are used. In one embodiment, the following algorithm is executed on each particle (using a shader):

```
vec2 pos = particle pos;
float life = particle life;
vec2 flow = flow vector at pos;
float prob = probability of particle appearing at pos; if (life
<= 0.0) {
    if (life < 0.0 || random( ) > prob) {
        pos = random vec2;
        life = 0.0;
    } else {
        life = 1.0;
    }
} else {
    // midpoint method
    flow = flow vector at half step forward;
    pos = full step forward;
    life -= (1.0 + length(flow.xy) * speedPenalty) * killRate;
}
```

Figure 10A:
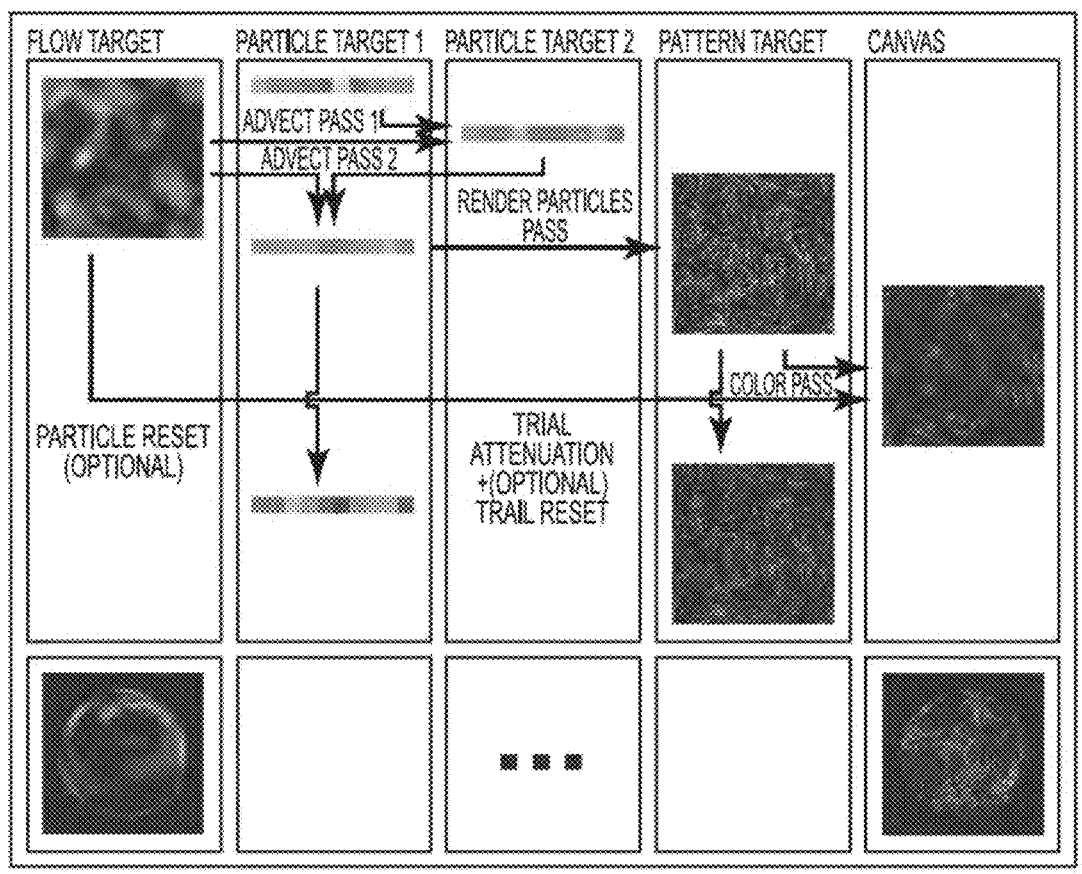
FIG. 10(a) shows one embodiment of a 2D particle algorithm.
Figure 10B:
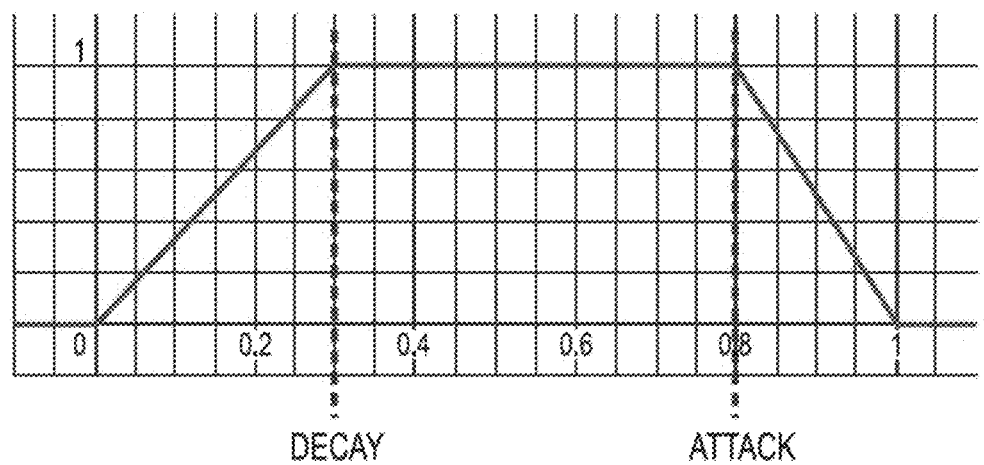
FIG. 10(b) shows a particle opacity attack/decay curve.

In the method of FIG. 10(a), each particle rendering pass takes particle target 1 as an input and then renders the particle onto a pattern target. In some embodiments, users can customize how particles are rendered by changing the sizes of the particles, the opacity curve's attack and decay edges, and the blend mode. Opacity curves can be important for reducing an undesired pop-in effect when resetting particles. If a particle appears with full brightness, it may not look smooth. To mitigate this issue, a simple linear attack and decay curve can be used, as shown in FIG. 10(b), where one embodiment of a particle opacity attack/decay curve is illustrated, and where Life goes from 1.0 to 0.0.

Line Integral Convolution

A line integral convolution technique may also be employed to describe and represent EGF flow fields. Line integral convolution techniques were introduced by Cabral and Leedom in 1993 as a means of displaying flow fields using noise. Starting with an image of noise (see, for example, the left-most panel of FIG. 11(b)), a special convolution technique is used to smear noise in the direction of flow. For each pixel, a streamline is calculated. Each location on the streamline is then averaged to generate a new color for that pixel (see, for example, the middle panel of FIG. 11(b)). The smear pattern is then colored to show magnitude. Although computationally intensive, the technique is ideal for implementation on a graphics card (using a shader) in combination with a real-time implementation in WebGL for display and presentation. In one embodiment, is for noise generation a 3D simplex noise algorithm by McEwan et al. (2012) can be used, which takes a 3D position in space and returns a smoothly changing pseudo-random value depending on where the 3D point lies on a simplex (tetrahedron) grid. Smoothly changing noise is important because it prevents aliasing when noise gets smeared.

Figure 11A:
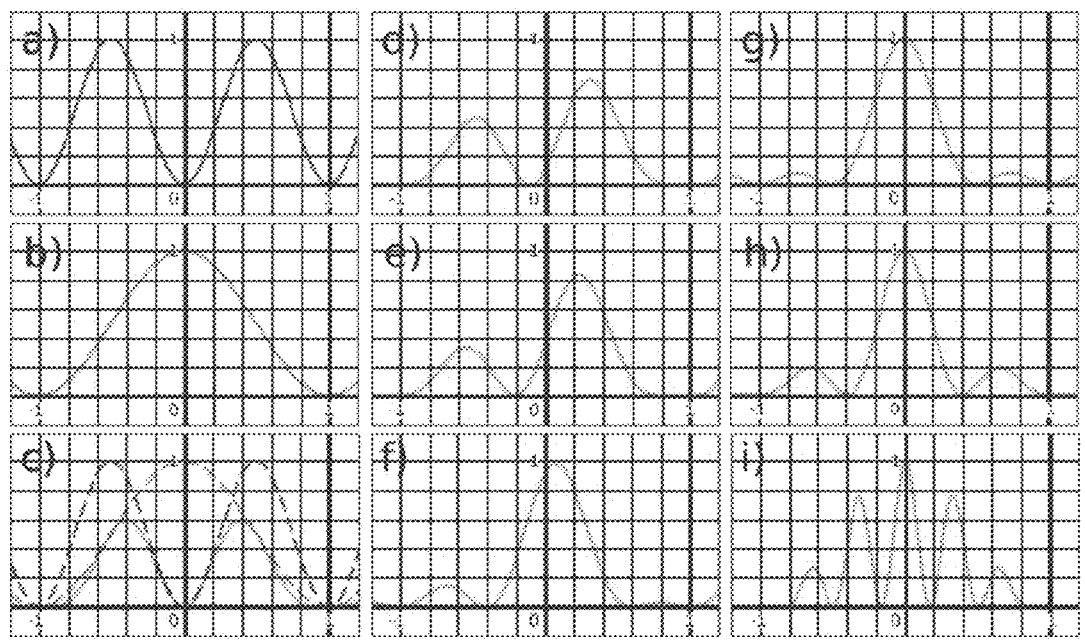
FIG. 11(a) shows function $f1$, function $f2$, function $f$, time $t$, and parameter $k$.
Figure 11B:
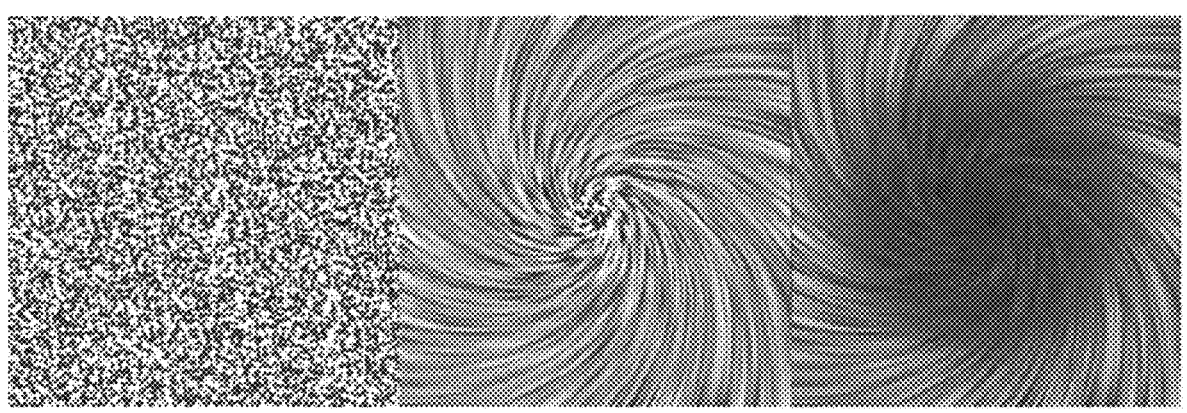
FIG. 11(b) shows various aspects according to one embodiment of a line integral convolution visualization method.

Referring now to FIG. 11(a), a line integral (also called a path integral, or a curve integral) is an integral of a scalar field along a given curve. In one embodiment, the scalar field is the noise texture, and the curve is a streamline. For each pixel, a streamline is calculated, both forwards and backwards (by advecting in a negative flow direction). The noise texture is then sampled along the streamline and averaged. Averaging can be accomplished in several ways. Usually, we want pixels closer to the original point to have more weight. For this purpose, and in one embodiment, a kernel function is used:

$$f(x) = \sin(\pi(kx+t))^2 \cos\left(\frac{\pi}{2}x\right)^2$$

where x is the position along the curve, interval [−1, 1], and is composed of two functions:

$$f_1(x) = \sin(\pi(kx+t))^2$$
$$f_2(x) = \cos\left(\frac{\pi}{2}x\right)^2$$

Function $f_1$ is used to create the animation of flow, because it shifts weight along the curve through time. Function $f2$ is used as a modulator to emphasize samples closer to the original point. See FIG. 11(a), where $f_1$ is shown in a), $f_2$ is shown in b), f (in red) is shown in c), d)

through g) show time t between 0 and 0.5, and g) through i) show parameter k (1.0, 1.5, and 2.0).

Figure 11C:
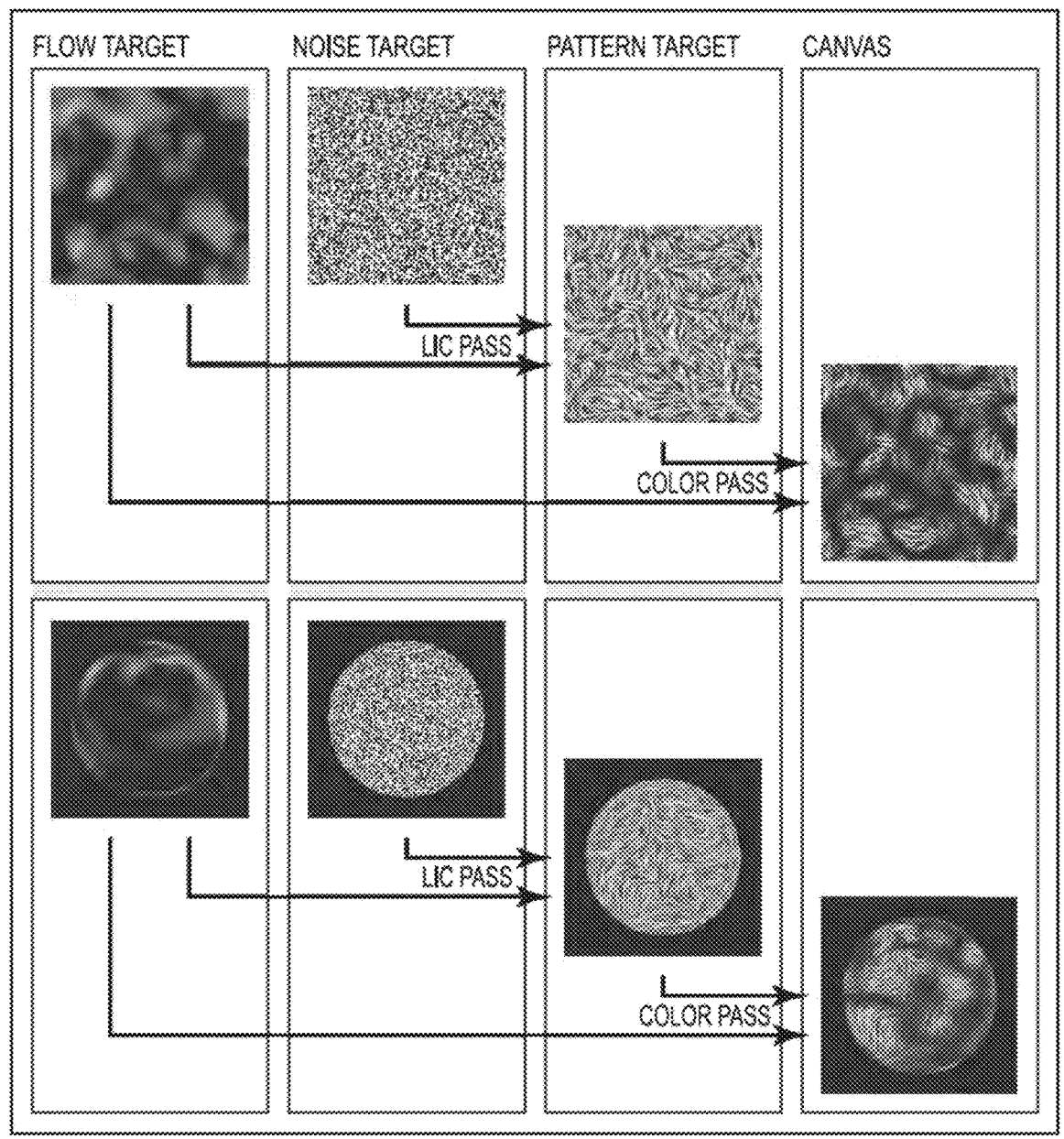
FIG. 11(c) illustrates one embodiment of a line integral convolution ("LIC") method or algorithm.

In one embodiment, the algorithm is implemented as a series of rendering passes for which 3 render targets are required: flow projection target, noise target, and pattern target. FIG. 11(c) illustrates one embodiment of a line integral convolution ("LIC") method or algorithm. The upper panel of FIG. 11(c) illustrates one embodiment of a 2D algorithm, while the lower panel in FIG. 11(c) illustrates one embodiment of a 3D algorithm. In each case, the first steps involve projecting flow and rendering noise. In a 2D case this amounts to simply rendering the flow field texture itself. Then, an "LIC pass" is performed to generate the pattern. Finally, a "color pass" is performed to mix pattern and pseudo color (i.e., color-mapping magnitude) of the projected flow field.

EXTENDING TO THREE DIMENSIONS (3D)

Projecting Flow

What is sought is to render a flow field as if it were wrapped around EP mapping assembly (or basket) 120 of catheter 110 in 3D. In one embodiment, this goal can be accomplished by mapping the flow field as a texture, and then projecting the flow vectors from a local space (uv) to a screen space using a pixel shader. The projected flow can then be employed to render an ordinary 2D version of flow visualization on a screen or monitor 148 (or other screen or monitor) for the user to view.

Figure 12A:
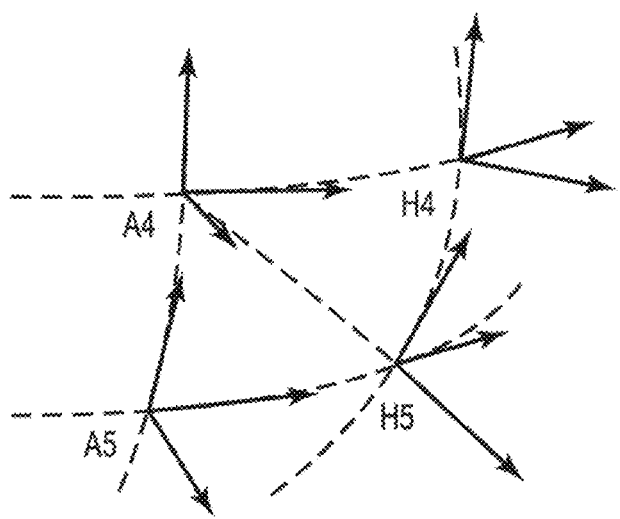
FIG. 12(a) shows points in space (A4, A5, H4, H5) and their corresponding vertices.

Referring now to FIG. 12(a), there are shown quad points in space (A4,A5,H4,H5) and their corresponding vertices. Vectors $\hat{u}$, $\hat{v}$ and $\hat{n}$ are red, green, and blue, respectively. Local space vectors (tangent $\hat{u}$, bitangent $\hat{v}$ and normal $\hat{n}$) are calculated for each triangle shown in FIG. 12(a) for triangle $A_5H_5A_4$ as follows:

$$u = \overrightarrow{A_5H_5}$$
$$v = \overrightarrow{A_5A_4}$$
$$n = \hat{u} \times \hat{v}$$

Then, in each vertex we sum and normalize neighboring triangles' $\hat{u}$, $\hat{v}$ and $\hat{n}$ so that each vertex has a normalized sum of all three vectors for all 6 neighboring triangles.

In flowProjectShader, $\hat{u}$ and $\hat{v}$ are used to transform the original 2D flow vector (x, y) to the 3D representation of the flow vector in local object space $f$, which is then transformed to a screen space using a projection matrix P and a model view matrix M. Keep in mind that this is a directional transformation, and therefore the homogeneous coordinate must be 0:

$$f = x\hat{u} + y\hat{v}$$

$$\vec{f}_s = PM \begin{bmatrix} f_x \\ f_y \\ f_z \\ 0 \end{bmatrix}$$

Figure 12B:
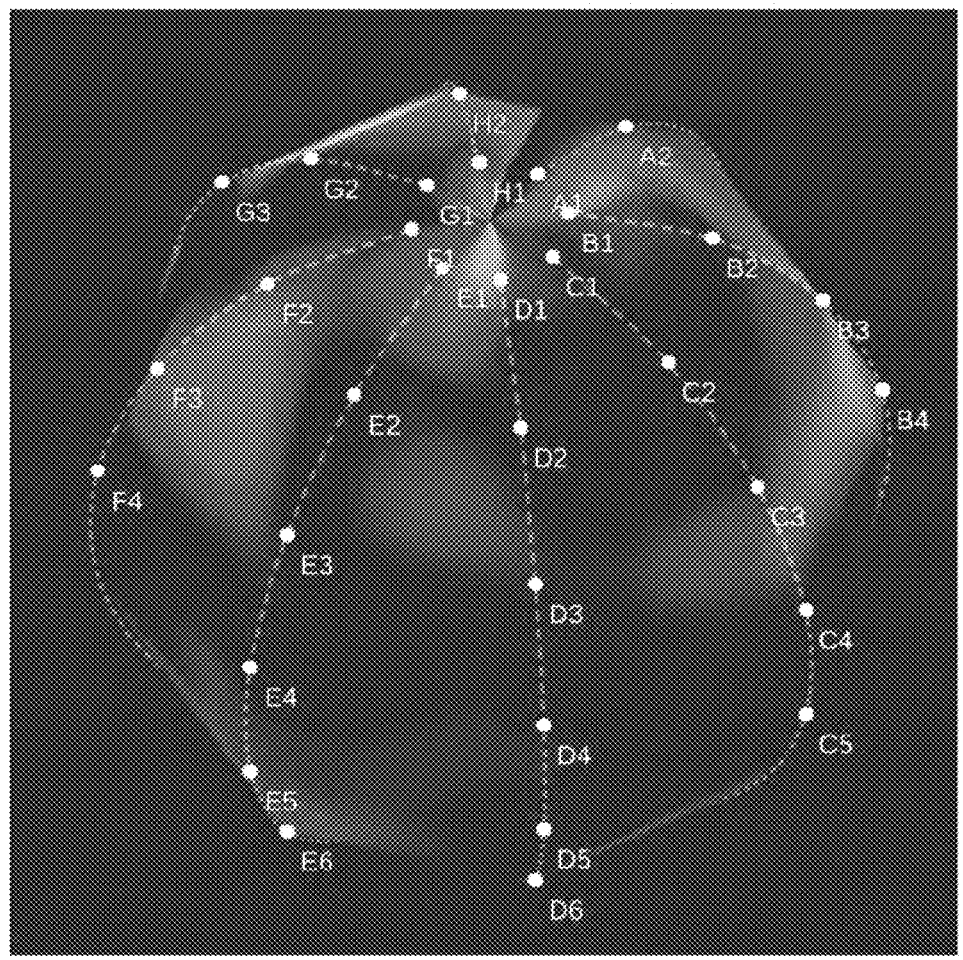
FIG. 12(b) shows one embodiment of EGF flow projected onto a linearly interpolated basket catheter.

FIG. 12(b) shows one embodiment of flow projected onto a linearly interpolated basket catheter. Red/green channels are projected $f_s x, f_s y$ components, respectively.

Surface Interpolation

Referring to preceding FIG. 12(b), some observers will note that the surface of the basket shown therein is linearly interpolated, which can create allasing artifacts and may not look pleasing to the eye. Although what a basket surface should look like in-between electrodes may be a matter of opinion or conjecture, it is reasonable to assume a basket surface should at least be represented by a smooth surface, meaning, for example, that it should exhibit at least $C^1$ continuity.

This constraint can be satisfied in an infinite number of ways. Here, and in one embodiment, a combination of centripetal Catmull-Rom curves (implemented by ThreeJS, mrdoob et al.) is used to interpolate basket's surface.

Figure 13A:
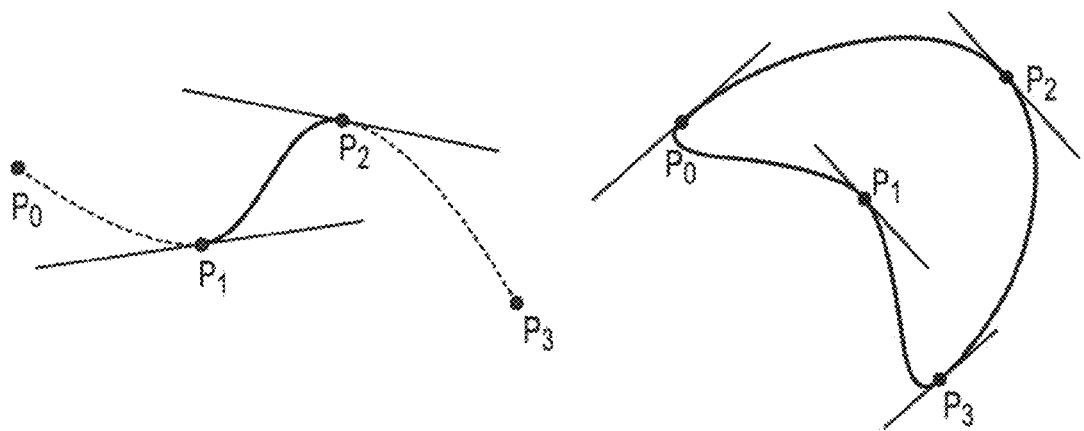
FIG. 13(a) shows a Catmull-Rom curve.

Referring now to FIG. 13(a), there is shown a Catmull-Rom curve, first described by Catmull and Rom (1974), which is defined by 4 control points $P_0, P_1, P_2, P_3$ and which produces a parametric curve going through (also called an interpolating spline) $P_1, P_2$. These points can be safely chained together while maintaining $C^1$ continuity by overlapping the first and last two points of each segment. It is important to use a centripetal version of the Catmull-Rom curve to ensure that no cusps or loops are formed. On the left of FIG. 13(a), an open version of a Catmull-Rom curve drawn through 4 points is shown, while the right of FIG. 13(a), a closed version of a Catmull-Rom curve drawn through 4 points is shown. Green lines in FIG. 13(a) represent tangents constructed by the difference of two neighboring points.

Figure 13B:
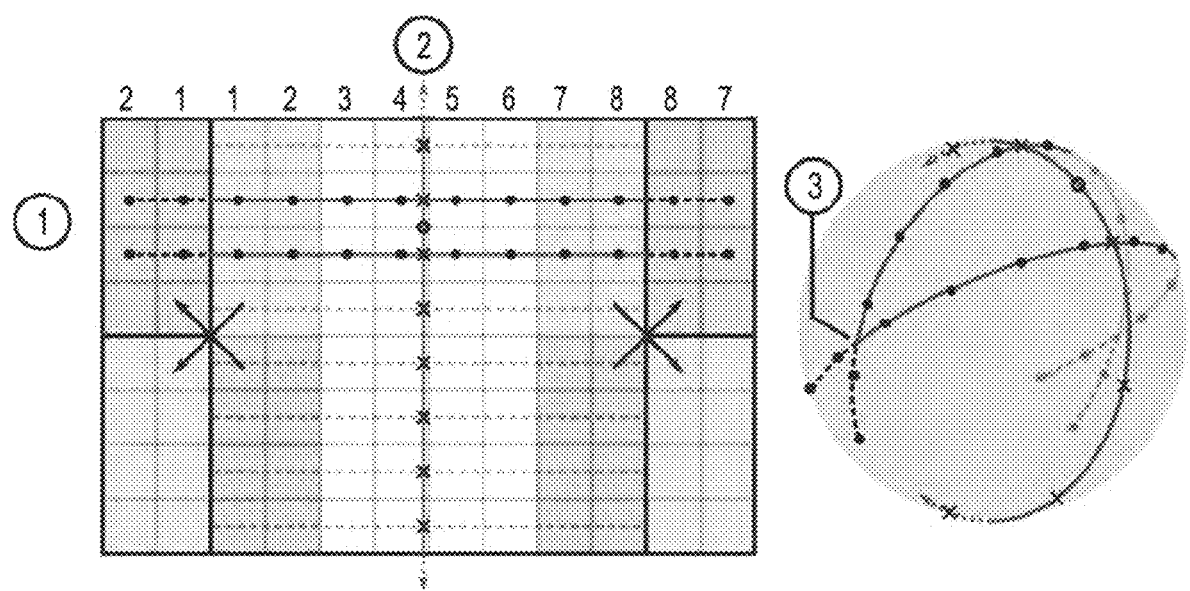
FIG. 13(b) shows a basket surface interpolation.
Figure 13C:
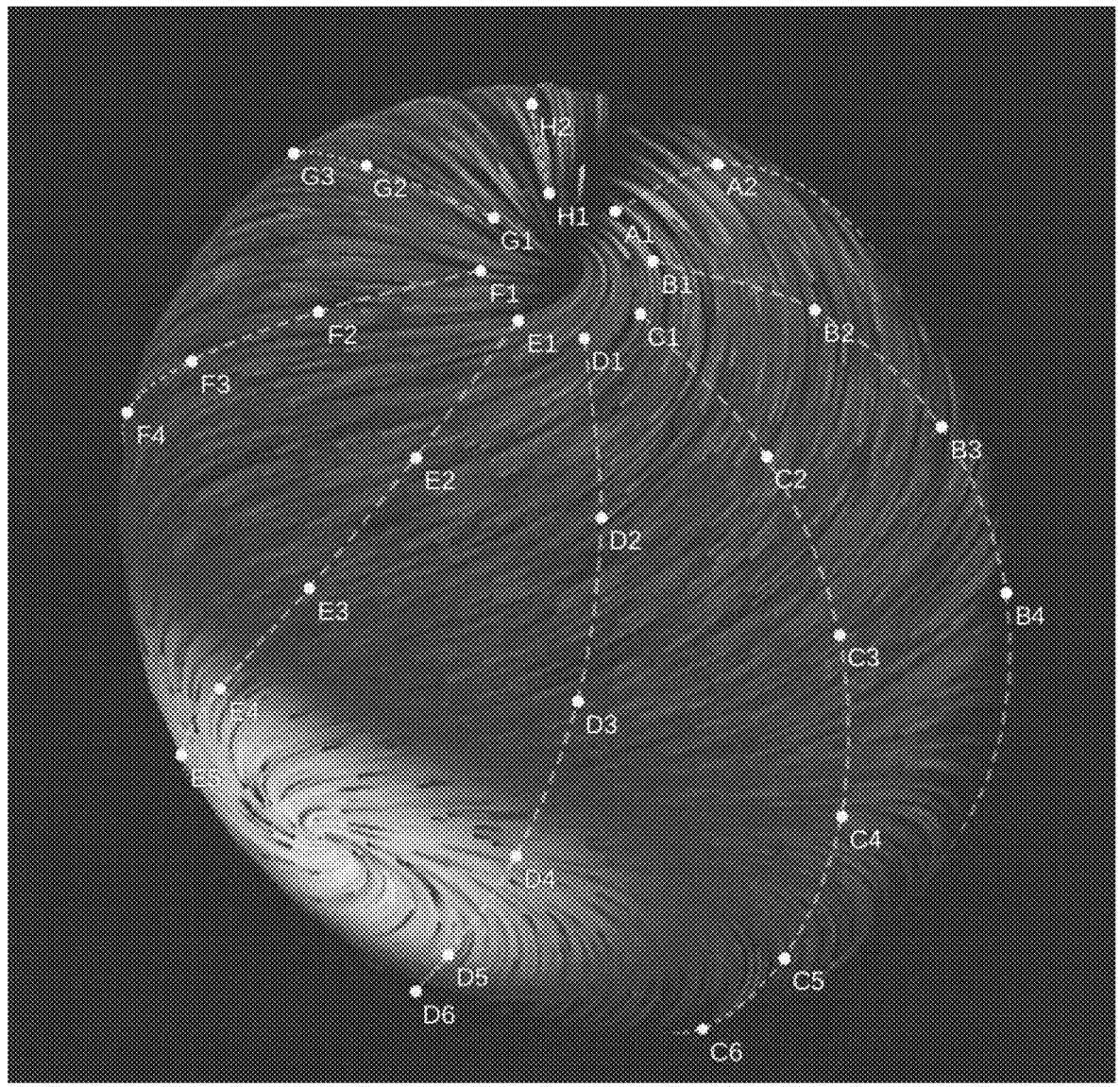
FIG. 13(c) shows one embodiment of a particle plot on a distorted basket geometry.

In one embodiment, interpolation is done in three stages. See FIG. 13(b). First, the basket's splines are subdivided using Catmull-Rom curves. Second, "rings" are constructed across splines, through the newly interpolated points using closed Catmull-Rom curves. Finally, the top and bottom common cap vertices are manually averaged and set to the same value to avoid rasterization mismatch due to small interpolation differences. In FIG. 13(b), basket surface interpolation is shown by: 1) interpolating splines; 2) interpolating across splines as closed loops, and 3) averaging the cap's common vertices to avoid rasterization mis-match. FIG. 13(c) shows one embodiment of a particle plot on a distorted basket geometry, where surface interpolation using Catmull-Rom techniques was employed. In the example of FIG. 13(c), there are 4 subdivisions splines, and 2 subdivisions along the splines.

EVALUATION

Correctness Testing

One important stage in developing Software for a Medical Device (SaMD) is testing. Software must be written that performs correctly. Since EGF flow visualization is primarily used to visualize the locations of sources, rotors, and sinks, proper functionality must be tested and verified thoroughly. One problem in particular that can be tricky to get right is the correct or proper mapping of flow. It has been found to be desirable to set 4 degrees of freedom: uv-mapping of the flow field (2 degrees), and mapping of individual vector components (2 degrees). Because different types of projections are employed in 2D views (vertical inverse) and 3D views (rotated by 90°), mapping is also carried out differently in these two cases.

Figure 14A:
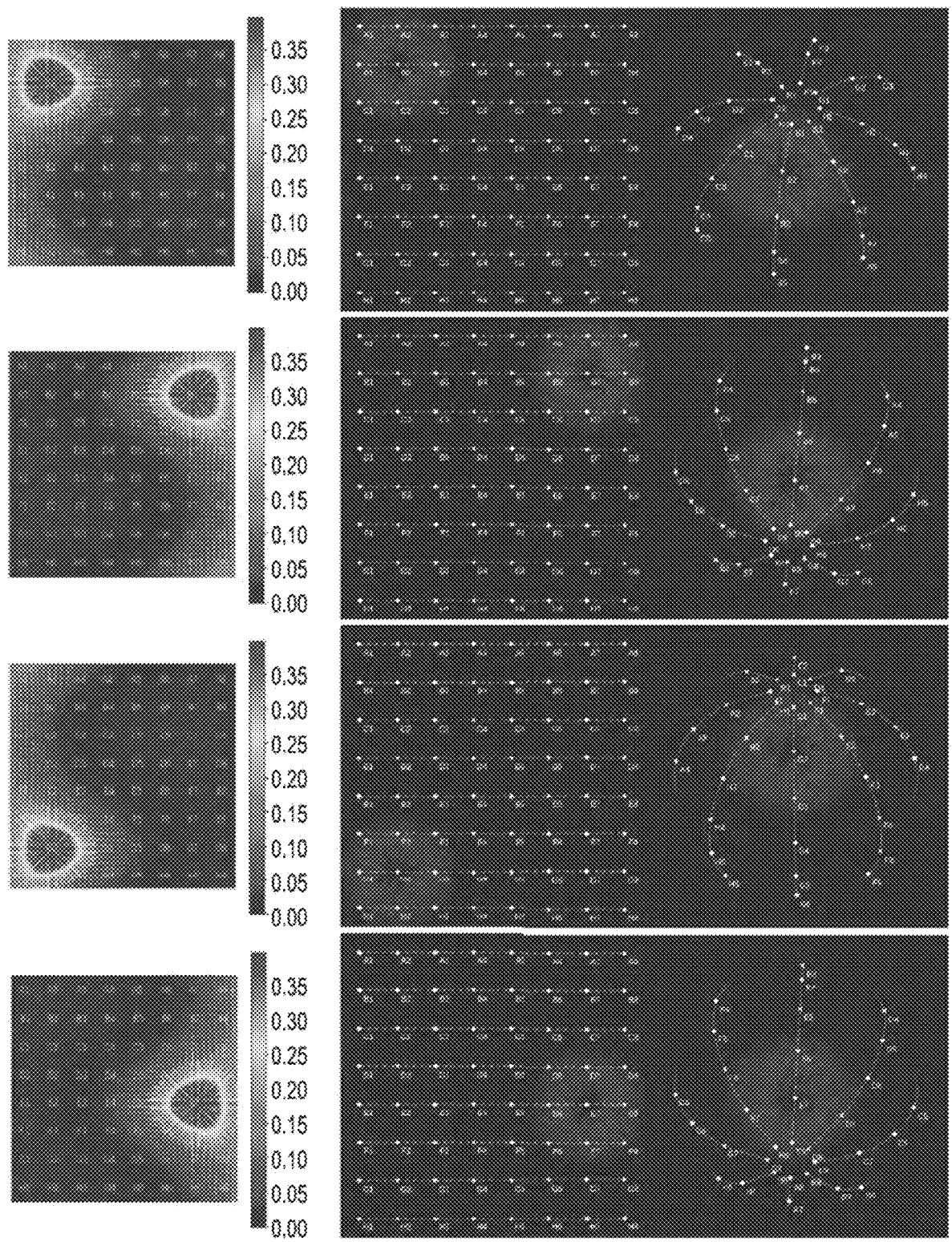
FIG. 14(a) shows the results of a unit test, where four different flow fields were created having sources at different locations.

FIG. 14(a) shows the results of a unit test, where 4 different flow fields were created with a source at different locations: B2, B7, G2, and E7. If any of the mappings were incorrect, we would either see sources in the wrong locations (wrong uv-mapping), or not see sources but instead saddles (e.g., points, rotors, sinks, and wrong vector component mapping). In FIG. 14(a), test cases are shown in order, from left to right: original Matplotlib plots (ground truth), 2D particle plot, and 3D particle plot. A probability mask is used to concentrate particles only in the source. Color bars in FIG. 14(a) simply show flow magnitude.

Even if a unit passes the foregoing test, that does not necessarily mean that the software will perform correctly when used in combination with an existing pipeline, or that the user will know how to use the software properly. Therefore, an end-to-end test is required to software test integration with an existing pipeline. For this purpose, a simple "mock" data generator is created. In one embodiment, a source or rotor is generated at a known location, and then it is determined whether the rotor or source appears at the proper location in the visualizer.

Figure 14B:
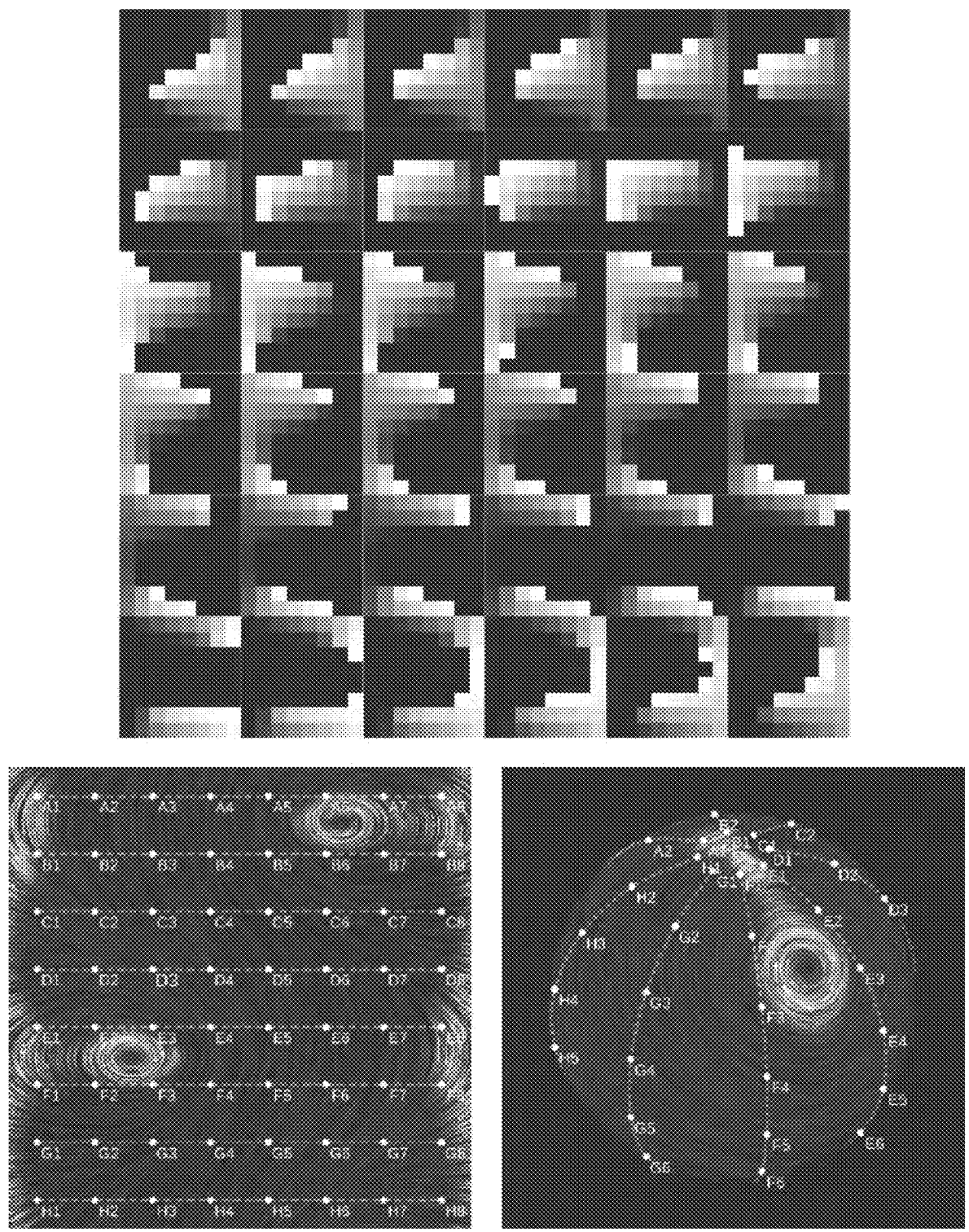
FIG. 14(b) shows one embodiment of an example dataset with a pure rotor having a certain axis of rotation and its corresponding resulting visualization.

In one embodiment, the generator uses 64 electrode locations and samples a 3D rotating wave defined as:

$$W(e,t)=\varphi(\alpha e \cdot \hat{y}+\beta a \tan 2(e \cdot \hat{z}, e \cdot \hat{x})),$$

where e is electrode location, $\varphi$ is the activation function (saw tooth used), $\hat{x}$, $\hat{y}$, $\hat{z}$ are basis vectors for the rotating wave, and $\alpha$, $\beta$ are divergence and rotation magnitude, respectively. FIG. 14(b) shows an example dataset with a pure rotor having an axis of rotation (0, 1, 1) and its corresponding resulting visualization.

Performance Testing

When testing software performance in a medical device context, it is important to note the environment in which the software will run. Typically, plenty of GPU power is available on hospital-deployed laptops, which usually have discrete GPUs on board. But the software and methods disclosed and described herein will also be used by doctors or scientists who use computers with potentially less powerful GPUs. Therefore, performance should be optimized to run at 30 frames or more per second (FPS), but 60 FPS should be easily reachable in many cases.

In some embodiments, both particle and LIC visualization methods utilize hardware acceleration through WebGL, mostly through heavy shader use. The geometry complexity itself is very minimal (<10 k triangles), so pixel shaders, fill rate, and latency are expected bottle-necks.

Figure 15A:
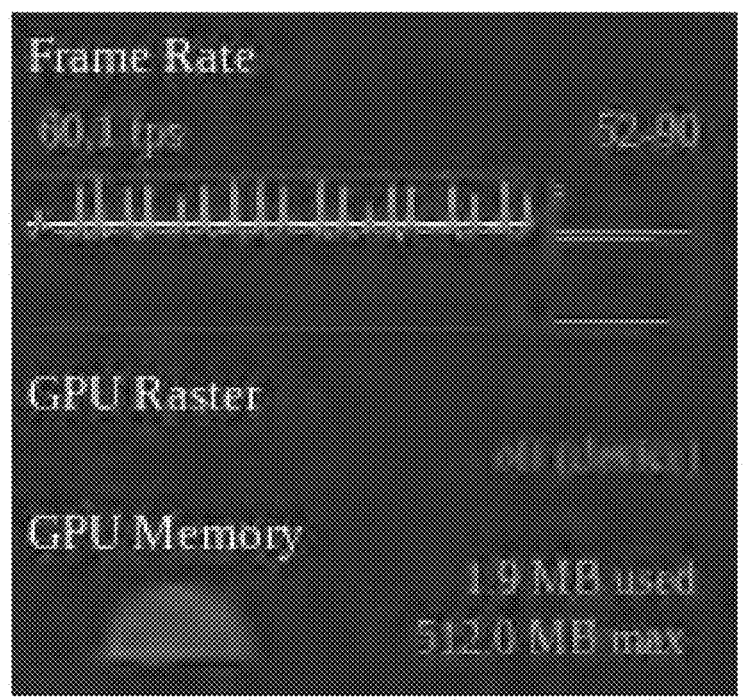
FIG. 15(a) shows Google Chrome's "FPS meter and memory usage.
Figure 15B:
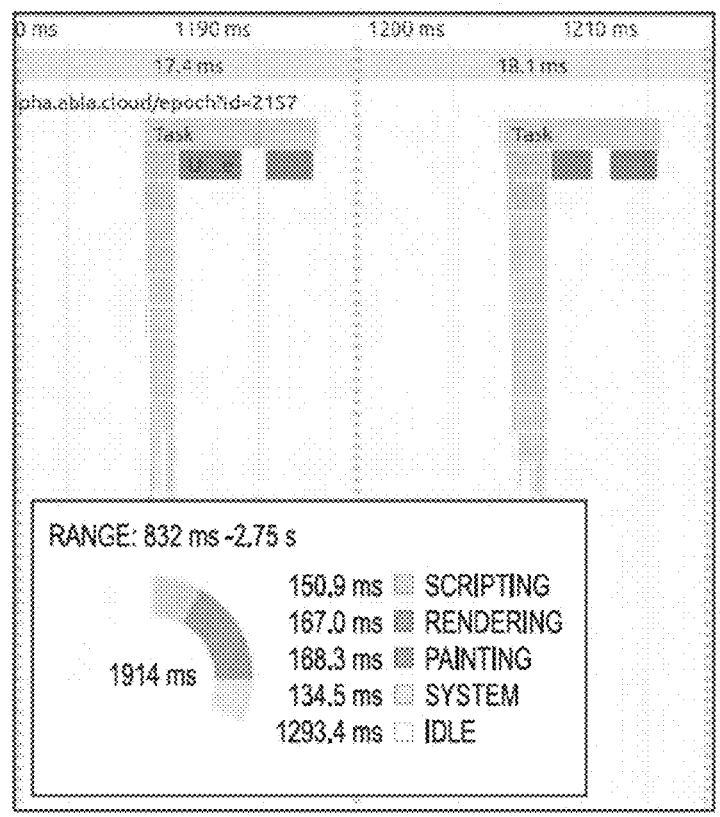
FIG. 15(b) shows Google Chrome's "Performance" tab and flame graph.

Software methods were therefore compared on a midrange laptop having the following configuration: Intel Core i7-8550U quad core CPU, Nvidia MX150 2 GB GPU, 16 GB RAM, and running Ubuntu 19.04. In WebGL, performance can was tracked in a few ways (using a Google Chrome browser):

1. Enabling "FPS meter." See FIG. 15(a), which shows Google Chrome's "FPS meter and memory usage. These visualizations used at most only a few dozen MB.
2. In dev tools, "Profiling" tab recorded all JavaScript callbacks and how long they took, also known as a flame graph. See FIG. 15(b), which shows Google Chrome's "Performance" tab and flame graph. The large column is flow visualization, while the other two blocks (dark purple and green) show HTML updating.
3. Entering about:tracing in a URL box and recording rendering activity. This method provides more advanced insights and timelines about individual calls made to the GPU.

When Quiver Plots, Streamline Plots, and Particle Plots were compared to one another, Particle Plot turned out to be a clear winner at a solid stutter-free 60 FPS, even at high resolutions and thousands of particles (1024×1024, 16 k particles). LIC plot, on the other hand, works well for smaller resolutions (50+ FPS at 400×400, 30+ FPS at 700×700), but generally scales poorly because of the large amount of work needed per pixel (calculating a whole streamline segment). Particle plot was also an initial favorite because of better perceived visual fidelity and intuitiveness (as tested with a target audience consisting of medical staff).

Particle Trails

Figure 16A:
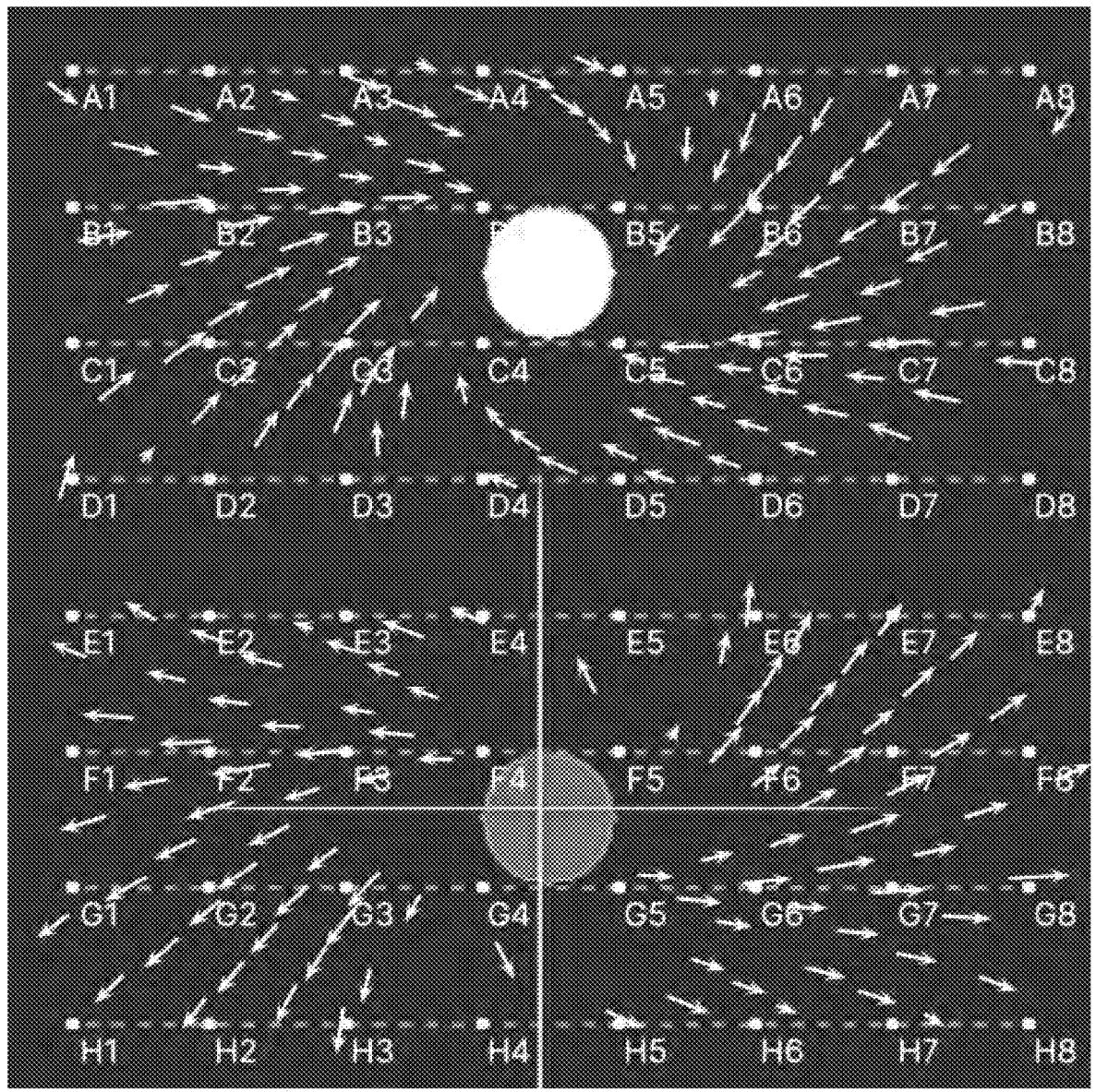
FIG. 16(a) shows an EGF flow field represented by arrows.

Finally, a fourth method of visualizing EGF fields was developed and tested: Particle Trails. FIG. 16(a) shows an EGF flow field represented by arrows, similar to what has been described and disclosed above. In FIG. 16(a), points of interest are highlighted (red: source; white: passive rotational phenomenon).

Another way to visualize an EGF field is with streamlines that are configured to go along vector fields. The problem with streamlines in this context is that it can be difficult for a user to discern the direction of flow. Arrows can be added to streamlines, but doing so often clutters the visualization.

Particle Trails provide an intuitive representation of flow fields that quickly illustrate the flow of action potentials in a patient's heart by moving particles across the screen such that they leave a fading trail. Particles and trails can be colored based on their location, starting point, velocity or other spatio-temporal metrics, such as fractionation or flow angle stability. The Particle Trails technique permits a qualitatively and quantitatively intuitive visualization of EGF fields to be achieved.

Each particle can be represented by a 1d float texture of length trailLen, where each element has 4-channels as follows:
  rgb→xyz
  a→age [0, trailLen−1]

Since trails need to start and end, they have different lengths at different points in a particle's life. To account for this, each trail row actually represents two particles: one still tracing and one that is dying, i.e. tracing has been stopped for one particle, and waiting for the trail to catch up in another particle. By way of non-limiting illustration, in one embodiment trail rows looks like the following for one cycle at consecutive points in time:

| t0 | -> | A7 | A6 | A5 | A4 | A3 | A2 | A1 | A0 |
| t1 | -> | B0 | A7 | A6 | A5 | A4 | A3 | A2 | A0 |
| t2 | -> | B1 | B0 | A7 | A6 | A5 | A4 | A3 | A0 |
| t3 | -> | B2 | B1 | B0 | A7 | A6 | A5 | A4 | A0 |
| t4 | -> | B3 | B2 | B1 | B0 | A7 | A6 | A5 | A0 |
| t5 | -> | B4 | B3 | B2 | B1 | B0 | A7 | A6 | A0 |
| t6 | -> | B5 | B4 | B3 | B2 | B1 | B0 | A7 | A0 |
| t7 | -> | B6 | B5 | B4 | B3 | B2 | B1 | B0 | A0 |
| t8 | -> | B7 | B6 | B5 | B4 | B3 | B2 | B1 | B0 |
| t9 | -> | C0 | B7 | B6 | B5 | B4 | B3 | B2 | B0 |

Notice that the last column stays the same as long as the next value to write does not have an age=0. This is because we want to remember the starting position of each particle.

Particle Buffer

To be more efficient, we pack trails into one as-square-as-possible 2d float texture of power-of-2 side lengths using an optimalTrailTextureSize function. The buffer texture might store multiple trails into one row because it is more efficient to create and update a square texture than a non-square texture. To go from a standard uv coordinate into this packed trail coordinate, use the trailuv glsl function.

Rendering Trails

Rendering the trails is basically drawing a single line through all of the rows. This of course, however, would not work because doing so would connect the beginning of one particle to the end of the other. Therefore, we employ a simple disconnection algorithm inside the render vertex shader:
render a vertex outside clipping space gl_Position.z=−1.0; (don't render it), if age==0.

Optimizing for Number of Points

Since rendering particle trails takes significant GPU power (texture access is expensive, and there may be tens of texture accesses per particle segment), a nice optimization that can be implemented is to not create a new trail point on every frame. Instead, we can animate a particle's movement for a few frames (a straight segment) before "remembering" the position as a new point. In effect this allows us to still animate particles on every frame and travel the same distance, but with fewer total points.

EXAMPLES

Figure 16B:
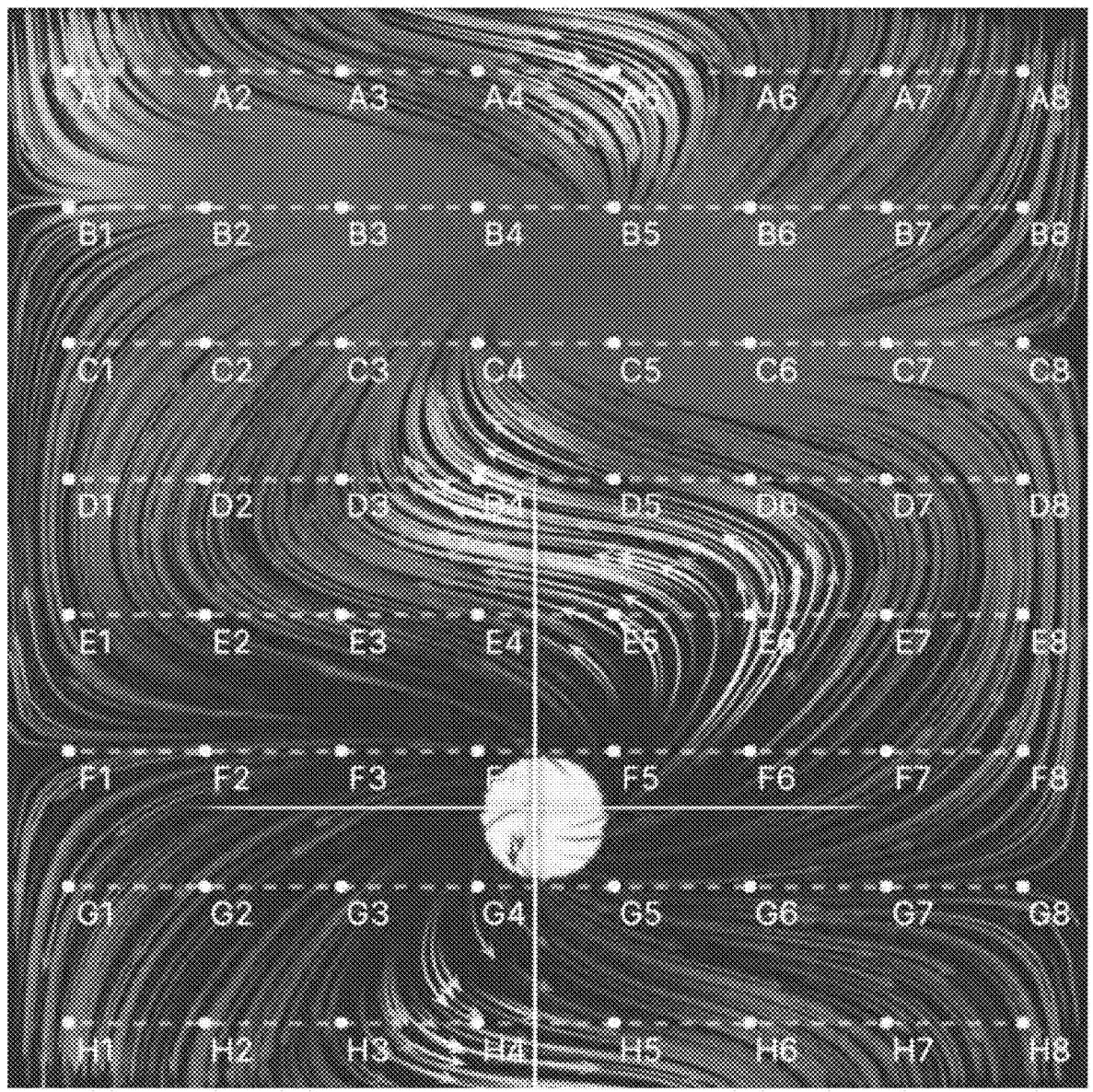
FIG. 16(b) a shows one embodiment of a still of an EGF field animation for particles with trails.

FIG. 16(b) a shows one embodiment of a still of an EGF field animation for particles with trails. Particles have an arrow head. In this embodiment, the color of the particles is derived from and associated with a velocity estimation.

Figure 16C:
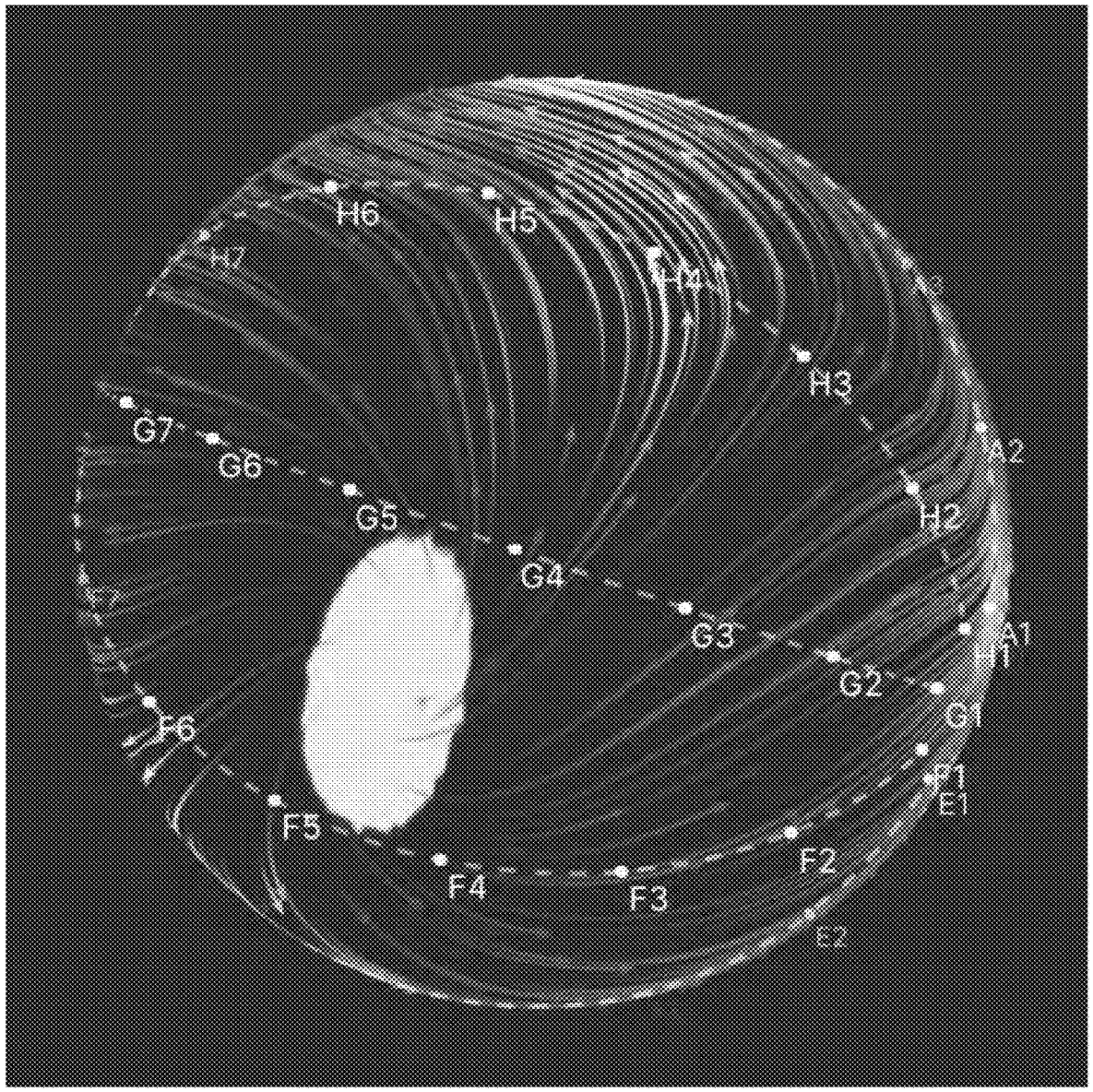
FIG. 16(c) shows one embodiment of a 3D projection and visualization of the same EGF particle animation as is shown in FIG. 16(b)

FIG. 16(c) shows one embodiment of a 3D projection and visualization of the same EGF particle animation as is shown in FIG. 16(b).

Figure 16D:
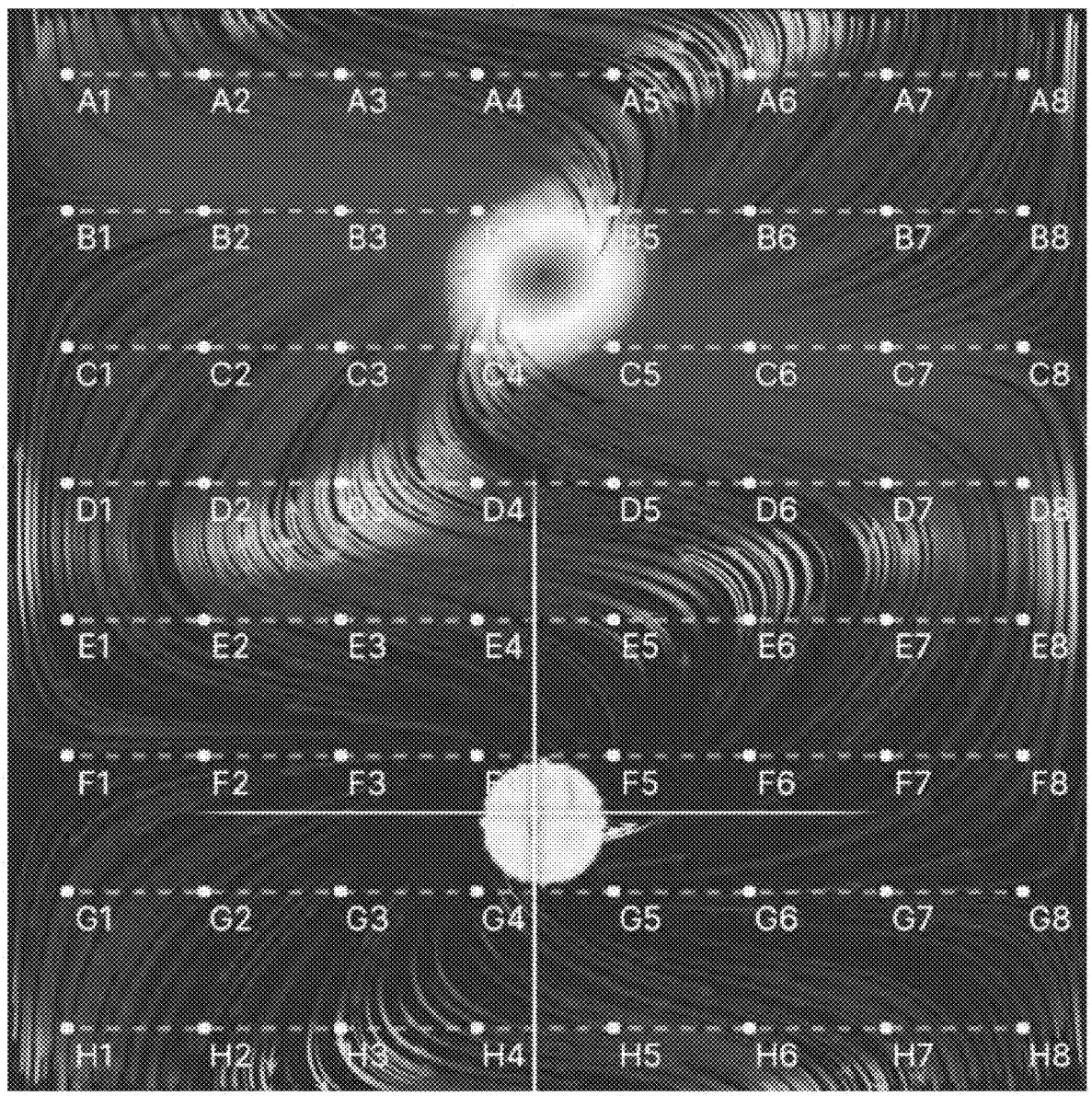
FIG. 16(d) shows another embodiment of an EGF field visualization, where the color of the particles is derived from a flow consistency map.

FIG. 16(d) shows another embodiment of an EGF field visualization, where the color of the particles is derived from a flow consistency map.

The problem of visualizing flow fields is well known in computer graphics. Summarized above are quiver plot, streamline plot, particle plot, line integral convolution, and particle trail visualization methods. Implementations of particle plots and LIC plots are presented, adapted for displaying EGF flow around a basket catheter. Both 2D and 3D approaches of each method are implemented. For a 3D approach, methods for projecting EGF flow and interpolating a surface are described, which work well for a reasonably distorted basket. Finally, described above are methods for testing software correctness and performance using mocked data (and showing expected results).

Initially, particle plot tended to emerge as a method preferred by end users (medical staff) because of its intuitiveness and better visual fidelity. It is also a better choice from a software performance perspective, since calculating convolutions in real time requires powerful hardware, especially for large resolutions. Subsequent development and testing, however, revealed that users preferred particle trail plot visualization techniques and software over the others described and disclosed herein.

The resulting flow visualization libraries and software described and disclosed herein can be implemented in a fast, compact Python library, based on extending Bokeh. The software can be easy to use with a Jupyter notebook, but may have limited applications in other fields because of its specialization. Further improvements can always be made, for example, in optimizing HTML performance, enabling improved specification and designation of 3D electrode locations from Python, additional tools such as 3D annotations, orientation indicators, and so on.

Various embodiments may include one or more of the following. A system configured to detect a location of a source of at least one cardiac rhythm disorder in a patient's heart, comprising an electrode mapping assembly comprising a plurality of electrodes and a plurality of arms or splines, the electrodes being mounted on or attached to the arms or splines, the electrode mapping assembly being configured to be deployed or opened inside the patient's heart such that at least some of the electrodes engage one or more sidewalls of the patients heart, each of the electrodes having a predetermined position on one of the arms or splines; a monitor or screen, and at least one computing device comprising at least one non-transitory computer readable medium configured to store instructions executable by at least one processor to determine the source and location of the cardiac rhythm disorder in the patient's heart; wherein the monitor or screen is operably connected to the computing device, and the computing device is configured to: (a) receive electrogram signals from the electrode mapping device while the electrode mapping assembly is deployed within the patient's heart to form a deployed 3D geometry of the electrode mapping assembly; (b) assign the predetermined positions of the electrodes on the mapping electrode assembly to their corresponding electrogram signals; (c) provide or generate a two-dimensional (2D) spatial map of the electrode positions; (d) for each or selected discrete times over which the electrogram signals are being processed, process the electrogram signals to generate a 2D electrographic flow map corresponding to the 2D spatial map of the electrode positions; and (e) project the generated 2D electrographic flow map onto a 3D representation of the deployed 3D geometry of the electrode mapping assembly on the monitor or screen to form a 3D electrographic flow map, the 3D electrographic flow map being configured to reveal the location of the source of the at least one cardiac rhythm disorder within the patient's heart so that a user can diagnose or treat the patient.

The system may further include one or more of: at least one of the 2D electrographic flow map and the 3D electrographic flow map comprisinglines and arrows representing individual vectors; the lines and arrows being represented by one or more of quiver plots, streamline plots, particle plots, particle trail plots, moving particle plots, and moving and fading particle plots; at least one of the 2D electrographic flow map and the 3D electrographic flow map being generated using convolution data processing techniques; the convolution data processing technique comprising line integral convolution; the 2D electrographic flow map being projected onto the 3D representation of the deployed 3D geometry on the monitor or screen by mapping the 2D electrographic flow map or flow field as one or more textures and projecting the flow vectors from the local space (uv) to screen space using a pixel shader; the 2D electrographic flow map being projected onto the 3D representation of the deployed 3D geometry on the monitor or screen after interpolating splines or arms of the electrode mapping assembly in the 2D spatial map, interpolating across splines as closed loops in the 2D spatial map, and averaging common vertices to prevent rasterization mismatches; mock rotor or source data being generated at a known location on the electrode mapping assembly and a user determines whether the mock rotor or source data are displayed correctly on the monitor or screen; the 2D or 3D electrographic flow map generated by the computing device comprising arrows or colors representative of directions of electrical potential propagation; the 2D or 3D electrographic flow map generated by the computing device comprising arrows or colors having attributes representative of velocities of electrical potential propagation; the 2D or 3D electrographic flow map generated by the computing device being configured to reveal the at least one cardiac rhythm disorder as an active rotor at the location; the 2D or 3D electrographic flow map generated by the computing device being configured to reveal a location of a passive rotor in the patient's heart; the 2D or 3D electrographic flow map generated by the computing device being configured to reveal a location of a focal point in the patient's heart; the 2D or 3D electrographic flow map generated by the computing device being configured to reveal a location of a breakthrough point in the patient's heart; the 2D or 3D electrographic flow map being generated by the computing device using at least one optical flow analysis technique; the at least one optical flow analysis technique being selected from the group consisting of a Horn-Schunck method, a Buxton-Buston method, a Black-Jepson method, a phase correlation method, a block-based method, a discrete optimization method, a Lucas-Kanade method, and a differential method of estimating optical flow; the electrode positions of the 3D representation of the deployed 3D geometry of the electrode mapping assembly being modified by the computing device based upon navigational or positional data corresponding to measured or sensed actual electrode positions; the navigational data being provided to the computing device by a medical navigation system, a computed tomography scanner, a magnetic resonance image scanner, or an X-ray fluoroscopy system; an ablation system comprising an ablation catheter, the ablation catheter being configured to ablate the patient's heart at the location and source of the cardiac rhythm disorder indicated by the velocity vector map; a catheter configured for insertion inside the patient's body and heart, the catheter comprising at a distal end thereof the mapping electrode assembly comprising a plurality of electrodes configured to sense and acquire from different locations inside the patient's heart the electrogram signals, each electrode having a predetermined position on the mapping electrode assembly associated therewith; the catheter being a basket catheter; an electrophysiological data acquisition device configured to receive and condition the signals provided by the electrodes to provide as an output therefrom the electrogram signals.

Various embodiments may still further include one or more of the following. A method of detecting a location of a source of at least one cardiac rhythm disorder in a patient's heart using a system comprising at least one computing device, the computing device comprising at least one non-transitory computer readable medium configured to store instructions executable by at least one processor to determine the source and location of the cardiac rhythm disorder in the patient's heart, the system further comprising a monitor or screen operably connected to the computing device and a mapping electrode assembly, the electrode mapping assembly comprising a plurality of electrodes and a plurality of arms or splines, the electrodes being mounted on or attached to the arms or splines, the electrode mapping assembly being configured to be deployed or opened inside the patient's heart such that at least some of the electrodes engage one or more sidewalls of the patients heart, each of the electrodes having a predetermined position on one of the arms or splines, the method comprising acquiring electrogram signals inside the patient's heart using the electrodes mounted on or attached to the mapping electrode assembly; using the computing device, assigning positions or identifiers for each of the electrodes to corresponding individual electrogram signals; using the computing device, providing or generating a two-dimensional (2D) spatial map of the electrode positions; using the computing device, processing the electrogram signals to generate a 2D electrographic flow map corresponding to the 2D spatial map of the electrode positions, and using the computing device, projecting the generated 2D electrographic flow map onto a 3D representation of the deployed 3D geometry of the electrode mapping assembly on the monitor or screen to form a 3D electrographic flow map, the 3D electrographic flow map being configured to reveal the location of the source of the at least one cardiac rhythm disorder so that a user can diagnose or treat the patient.

The method may yet further include one or more of: inserting a catheter inside the patient's body and heart, the catheter comprising at a distal end thereof the mapping electrode assembly; estimating wave shapes when generating the 2D or 3D electrographic flow map; generating one or more electrographic flow maps using Green's function; generating one or more electrographic flow maps using at least one optical flow analysis technique; the at least one optical flow analysis technique being selected from the group consisting of a Horn-Schunck method, a Buxton-Buston method, a Black-Jepson method, a phase correlation method, a block-based method, a discrete optimization method, a Lucas-Kanade method, and a differential method of estimating optical flow; interpolating or estimating values for positions in between measured or calculated map or grid values corresponding to one or more of the electrogram signals; modifying the electrode positions in the 2D or 3D representations based upon navigational or positional data corresponding to measured or sensed actual electrode positions; providing the navigational or positional data from a medical navigation system, a computed tomography scanner, a magnetic resonance image scanner, or an X-ray fluoroscopy system; providing at least one of the 2D electrographic flow map and the 3D electrographic flow map using lines and arrows to represent individual vectors; is the lines and arrows being represented by one or more of quiver plots, streamline plots, particle plots, particle trail plots, moving particle plots, and moving and fading particle plots; at least one of the 2D electrographic flow map and the 3D electrographic flow map being generated using convolution data processing techniques; the convolution data processing technique comprising line integral convolution; the 2D electrographic flow map being projected onto the 3D representation of the deployed 3D geometry on the monitor or screen by mapping the 2D electrographic flow map or flow field as one or more textures and projecting the flow vectors from the local space (uv) to screen space using a pixel shader; the 2D electrographic flow map being projected onto the 3D representation of the deployed 3D geometry on the monitor or screen after interpolating splines or arms of the electrode mapping assembly in the 2D spatial map, interpolating across splines as closed loops in the 2D spatial map, and averaging common vertices to prevent rasterization mismatches; mock rotor or source data being generated at a known location on the electrode mapping assembly and a user determines whether the mock rotor or source data are displayed correctly on the monitor or screen.

These and other aspects, features, advantages, and characteristics of better visualizing EGF fields and cardiac rhythm disorders in patients' hearts generally, and determining improved therapies to deliver to such patients, are described in further detail in the appended drawings and descriptions.

Various embodiments of EGF visualization techniques beyond those described and disclosed explicitly herein are contemplated, including, but not limited to, EGF visualization techniques other than quiver plot, streamline plot, particle plot, line integral convolution, and particle trail visualization methods.

What have been described above are examples and embodiments of the devices and methods described and disclosed herein. It is, of course, not possible to describe every conceivable combination of components or methodologies for purposes of describing the invention, but one of ordinary skill in the art will recognize that many further combinations and permutations of the devices and methods described and disclosed herein are contemplated and possible.

Accordingly, the devices and methods described and disclosed herein are intended to embrace all such alterations, modifications and variations that fall within the scope of the appended claims. In the claims, unless otherwise indicated, the article "a" is to refer to "one or more than one."

The foregoing outlines features of several embodiments so that those skilled in the art may better understand the detailed description set forth herein. Those skilled in the art will now understand that many different permutations, combinations and variations of EGF visualization methods will fall within the scope of the various embodiments. Those skilled in the art should appreciate that they may readily use the present disclosure as a basis for designing or modifying other software, methods, techniques, processes, hardware, and/or structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

After having read and understood the present specification, those skilled in the art will now understand and appreciate that the various embodiments described herein provide solutions to long-standing problems, not only in the use of electrophysiological mapping systems and cardiac ablation systems, but in visualizing EGF fields generally.

APPENDICES

Bibliography

Barbara Bellmann, Tina Lin, Peter Ruppersberg, Marit Zettwitz, Selma Guttmann, Verena Tscholl, Patrick Nagel, Mattias Roser, Ulf Landmesser, and Andreas Rillig. Identification of active atrial fibrillation sources and their discrimination from passive rotors using electrographical flow mapping. Clinical Research in Cardiology, 107(11): 1021-1032, 2018.

Brian Cabral and Leith Casey Leedom. Imaging vector fields using line integral convolution. Technical report, Lawrence Livermore National Lab., Calif. (United States), 1993.

Edwin Catmull and Raphael Rom. A class of local interpolating splines. U Computer aided geometric design, stranice 317-326. Elsevier, 1974.

Ian McEwan, David Sheets, Mark Richardson, and Stefan Gustayson. Efficient computational noise in glsl. Journal of Graphics Tools, 16(2):85-94, 2012.

mrdoob et al. Threejs. https://threejs.org/docs/. Accessed: 2019-06-21.

Paulus, Stefano Benussi, Kirchhof, Dipak Kotecha, Anders Ahlsson, Dan Atar, Bar-bara Casadei, Manuel Castella, Hans-Christoph Diener, Hein Heidbuchel, Jeroen Hendriks, et al. 2016 esc guidelines for the management of atrial fibrillation developed in collaboration with eacts. European journal of cardio-thoracic surgery, 50 (5):e1-e88, 2016.

Each of the above-listed publications is incorporated by reference herein, each in its respective entirety, pursuant to an Information Disclosure Statement (IDS) and corresponding copies of the foregoing publications submitted on even date herewith.

Types of Field Lines

Streamlines include, but are not necessarily limited to, a family of curves that are instantaneously tangent to the velocity vector of the flow field.

Streaklines include, but are not necessarily limited to, the locations of points of all the fluid particles that have passed continuously through a particular spatial point in the past.

Pathlines include, but are not necessarily limited to, the trajectories that individual fluid particles follow. These can be thought of as "recording" the path of a fluid element in the flow over a certain period.

Timelines include, but are not necessarily limited to, the lines formed by an ordered set of fluid particles that were marked in the past, creating a line or a curve that gets displaced in time as the particles move.

In time-invariant (steady) flow, streamlines, streaklines and pathlines typically coincide.

Parameters

1. Common parameters to all visualizer models are:

show_param_gui Set to true to show parameter GUI.

param_gui_closedSet to true to close parameter GUI on load.

param_gui_location String: "right", "bottom" or "auto".

normalizeSet to true to normalize the flow field before render.

time_scale Usually 1/60s, specifies the "speed" of the animation without influencing the look too much.

source Data source of type ColumnDataSource containing the flow field data.

flowTarget column name where flow field data is found in the source.

use_pseudo_colorSet to true to color the flow field using custom color instead of magnitude.

color_mapName of any Bokeh color palette used for foreground.

color_map_lowLow cutoff for color palette.

color_map_highHigh cutoff for color palette.

bg_color_mapName of any Bokeh color palette used for background.

atrium"LA" or "RA". If specified "LA", the basket will rotate by 90° around z axis to mimic the orientation in real life.

slider Data source can contain multiple flow maps, and a slider can be used to flip through them.

animation_delta_time If specified >0, it will flip through the flow maps using the given delta time.

2. Common "particle plot" parameters:
particle_count Number of particles
image_half_life Time it takes for trails to lose 50% brightness.
step_sizeSize of the "step" a particle takes on unit magnitude flow in one second.
kill_rate Rate at which particles' life gets reduced.
speed_penaltyAdditional kill rate increase for particles in fast-moving flow.
attack_edgeNumeric value in [0,1] range representing when parti-cles achieve highest brightness.
release_edgeNumeric value in [0,1] range representing when parti-cles' brightness starts to fall back to 0.
particle_sizeSize of the particles in pixels.
3. Common LIC plot parameters:
noise_scaleScale of the simplex noise. Higher values means smaller noise specks.
noise_thr_low Threshold for noise output to be 0.
noise_thr_high Threshold for the noise output to be 1.
step_size Step size done by midpoint method.
kernel_coefNumber of periods in animation kernel.

We claim:

1. A system configured to detect a location of a source of at least one cardiac rhythm disorder in a patient's heart, comprising:
(i) an electrode mapping assembly comprising a plurality of electrodes and a plurality of arms or splines, the electrodes being mounted on or attached to the arms or splines, the electrode mapping assembly being configured to be deployed or opened inside the patient's heart such that at least some of the electrodes engage one or more sidewalls of the patient's heart, each of the electrodes having a predetermined position on one of the arms or splines;
(ii) a monitor or screen, and
(iii) at least one computing device comprising at least one non-transitory computer readable medium configured to store instructions executable by at least one processor to determine the source and location of the cardiac rhythm disorder in the patient's heart;
wherein the monitor or screen is operably connected to the computing device, and the computing device is configured to: (a) receive electrogram signals from the electrode mapping assembly while the electrode mapping assembly is deployed within the patient's heart to form a deployed 3D geometry of the electrode mapping assembly; (b) assign the predetermined positions of the electrodes on the mapping electrode assembly to their corresponding electrogram signals; (c) provide or generate a two-dimensional (2D) spatial map of the electrode positions; (d) for each or selected discrete times over which the electrogram signals are being processed, process the electrogram signals to generate a 2D electrographic flow map corresponding to the 2D spatial map of the electrode positions; (e) project the generated 2D electrographic flow map onto a 3D representation of the deployed 3D geometry of the electrode mapping assembly on the monitor or screen to form a 3D electrographic flow map, the 3D electrographic flow map being configured to reveal the location of the source of the at least one cardiac rhythm disorder within the patient's heart so that a user can diagnose or treat the patient, and at least one of: (f) project the 2D electrographic flow map onto the 3D representation of the deployed 3D geometry on the monitor or screen by mapping the 2D electrographic flow map or flow field as one or more textures and projecting the flow vectors from the local space (uv) to screen space using a pixel shader, and (q) project the 2D electrographic flow map onto the 3D representation of the deployed 3D geometry on the monitor or screen after interpolating splines or arms of the electrode mapping assembly in the 2D spatial map, interpolating across splines as closed loops in the 2D spatial map, and averaging common vertices to prevent rasterization mismatches.

2. The system of claim 1, wherein at least one of the 2D electrographic flow map and the 3D electrographic flow map comprises lines and arrows representing individual vectors.

3. The system of claim 2, wherein the lines and arrows are represented by one or more of quiver plots, streamline plots, particle plots, particle trail plots, moving particle plots, and moving and fading particle plots.

4. The system of claim 1, wherein at least one of the 2D electrographic flow map and the 3D electrographic flow map is generated using convolution data processing techniques.

5. The system of claim 4, wherein the convolution data processing technique comprises line integral convolution.

6. The system of claim 1, wherein mock rotor or source data are generated at a known location on the electrode mapping assembly and a user determines whether the mock rotor or source data are displayed correctly on the monitor or screen.

7. The system of claim 1, wherein the 2D or 3D electrographic flow map generated by the computing device comprises arrows or colors representative of directions of electrical potential propagation.

8. The system of claim 1, wherein the 2D or 3D electrographic flow map generated by the computing device comprises arrows or colors having attributes representative of velocities of electrical potential propagation.

9. The system of claim 1, wherein the 2D or 3D electrographic flow map generated by the computing device is configured to reveal the at least one cardiac rhythm disorder as an active rotor at the location.

10. The system of claim 1, wherein the 2D or 3D electrographic flow map generated by the computing device is configured to reveal a location of a passive rotor in the patient's heart.

11. The system of claim 1, wherein the 2D or 3D electrographic flow map generated by the computing device is configured to reveal a location of a focal point in the patient's heart.

12. The system of claim 1, wherein the 2D or 3D electrographic flow map generated by the computing device is configured to reveal a location of a breakthrough point in the patient's heart.

13. The system of claim 1, wherein the 2D or 3D electrographic flow map is generated by the computing device using at least one optical flow analysis technique.

14. The system of claim 13, wherein the at least one optical flow analysis technique is selected from the group consisting of a Horn-Schunck method, a Buxton-Buston method, a Black-Jepson method, a phase correlation method, a block-based method, a discrete optimization method, a Lucas-Kanade method, and a differential method of estimating optical flow.

15. The system of claim 14, wherein the navigational data are provided to the computing device by a medical navigation system, a computed tomography scanner, a magnetic resonance image scanner, or an X-ray fluoroscopy system.

16. The system of claim 1, wherein the electrode positions of the 3D representation of the deployed 3D geometry of the electrode mapping assembly are modified by the computing device based upon navigational or positional data corresponding to measured or sensed actual electrode positions.

17. The system of claim 1, further comprising an ablation system comprising an ablation catheter, the ablation catheter being configured to ablate the patient's heart at the location and source of the cardiac rhythm disorder indicated by the velocity vector map.

18. The system of claim 1, further comprising a catheter configured for insertion inside the patient's body and heart, the catheter comprising at a distal end thereof the electrode mapping assembly comprising the plurality of electrodes configured to sense and acquire from different locations inside the patient's heart the electrogram signals, each electrode having a predetermined position on the electrode mapping assembly associated therewith.

19. The system of claim 1, wherein the catheter is a basket catheter.

20. The system of claim 1, further comprising an electrophysiological data acquisition device configured to receive and condition the signals provided by the electrodes to provide as an output therefrom the electrogram signals.

21. A method of detecting a location of a source of at least one cardiac rhythm disorder in a patient's heart using a system comprising at least one computing device, the computing device comprising at least one non-transitory computer readable medium configured to store instructions executable by at least one processor to determine the source and location of the cardiac rhythm disorder in the patient's heart, the system further comprising a monitor or screen operably connected to the computing device and an electrode mapping assembly, the electrode mapping assembly comprising a plurality of electrodes and a plurality of arms or splines, the electrodes being mounted on or attached to the arms or splines, the electrode mapping assembly being configured to be deployed or opened inside the patient's heart such that at least some of the electrodes engage one or more sidewalls of the patient's heart, each of the electrodes having a predetermined position on one of the arms or splines, the method comprising:
  (a) acquiring electrogram signals inside the patient's heart using the electrodes mounted on or attached to the mapping electrode assembly;
  (b) using the computing device, assigning positions or identifiers for each of the electrodes to corresponding individual electrogram signals;
  (c) using the computing device, providing or generating a two-dimensional (2D) spatial map of the electrode positions;
  (d) using the computing device, processing the electrogram signals to generate a 2D electrographic flow map corresponding to the 2D spatial map of the electrode positions;
  (e) using the computing device, projecting the generated 2D electrographic flow map onto a 3D representation of the deployed 3D geometry of the electrode mapping assembly on the monitor or screen to form a 3D electrographic flow map, the 3D electrographic flow map being configured to reveal the location of the source of the at least one cardiac rhythm disorder so that a user can diagnose or treat the patient, and at least one of:
  (f) projecting the 2D electrographic flow map onto the 3D representation of the deployed 3D geometry on the monitor or screen by mapping the 2D electrographic flow map or flow field as one or more textures and projecting the flow vectors from the local space (uv) to screen space using a pixel shader, and
  (q) projecting the 2D electrographic flow map onto the 3D representation of the deployed 3D geometry on the monitor or screen after interpolating splines or arms of the electrode mapping assembly in the 2D spatial map, interpolating across splines as closed loops in the 2D spatial map, and averaging common vertices to prevent rasterization mismatches.

22. The method of claim 21, further comprising inserting a catheter inside the patient's body and heart, the catheter comprising at a distal end thereof the mapping electrode assembly.

23. The method of claim 21, further comprising estimating wave shapes when generating the 2D or 3D electrographic flow map.

24. The method of claim 21, further comprising generating one or more electrographic flow maps using Green's function.

25. The method of claim 21, further comprising generating one or more electrographic flow maps using at least one optical flow analysis technique.

26. The method of claim 25, wherein the at least one optical flow analysis technique is selected from the group consisting of a Horn-Schunck method, a Buxton-Buston method, a Black-Jepson method, a phase correlation method, a block-based method, a discrete optimization method, a Lucas-Kanade method, and a differential method of estimating optical flow.

27. The method of claim 21, further comprising interpolating or estimating values for positions in between measured or calculated map or grid values corresponding to one or more of the electrogram signals.

28. The method of claim 21, further comprising modifying the electrode positions in the 2D or 3D representations based upon navigational or positional data corresponding to measured or sensed actual electrode positions.

29. The method of claim 28, further comprising providing the navigational or positional data from a medical navigation system, a computed tomography scanner, a magnetic resonance image scanner, or an X-ray fluoroscopy system.

30. The method of claim 21, further comprising providing at least one of the 2D electrographic flow map and the 3D electrographic flow map using lines and arrows to represent individual vectors.

31. The method of claim 30, wherein the lines and arrows are represented by one or more of quiver plots, streamline plots, particle plots, particle trail plots, moving particle plots, and moving and fading particle plots.

32. The method of claim 21, wherein at least one of the 2D electrographic flow map and the 3D electrographic flow map is generated using convolution data processing techniques.

33. The method of claim 32, wherein the convolution data processing technique comprises line integral convolution.

34. The method of claim 21, wherein mock rotor or source data are generated at a known location on the electrode mapping assembly and a user determines whether the mock rotor or source data are displayed correctly on the monitor or screen.

* * * * *